(12) United States Patent
Lipkens et al.

(10) Patent No.: US 10,953,436 B2
(45) Date of Patent: Mar. 23, 2021

(54) ACOUSTOPHORETIC DEVICE WITH PIEZOELECTRIC TRANSDUCER ARRAY

(71) Applicant: FloDesign Sonics, Inc., Wilbraham, MA (US)

(72) Inventors: Bart Lipkens, Hampden, MD (US); Jason Dionne, Simsbury, CT (US)

(73) Assignee: FloDesign Sonics, Inc., Wilbraham, MA (US)

( * ) Notice: Subject to any disclaimer, the term of this patent is extended or adjusted under 35 U.S.C. 154(b) by 534 days.

(21) Appl. No.: 15/285,349

(22) Filed: Oct. 4, 2016

(65) Prior Publication Data

US 2017/0066015 A1 Mar. 9, 2017

Related U.S. Application Data

(63) Continuation-in-part of application No. 14/708,035, filed on May 8, 2015, now Pat. No. 9,457,302, which
(Continued)

(51) Int. Cl.
*B06B 1/06* (2006.01)
*B01D 43/00* (2006.01)
(Continued)

(52) U.S. Cl.
CPC ............ *B06B 1/0622* (2013.01); *B01D 43/00* (2013.01); *C12M 47/02* (2013.01); *H01L 41/047* (2013.01); *H01L 41/0533* (2013.01); *H01L 41/09* (2013.01)

(58) Field of Classification Search
CPC .............. G01H 17/00; G01N 15/1459; G01N 2001/4094; G01N 2015/142;
(Continued)

(56) References Cited

U.S. PATENT DOCUMENTS

| 2,473,971 A | 6/1949 | Ross |
| 2,667,944 A | 2/1954 | Crites |

(Continued)

FOREIGN PATENT DOCUMENTS

| DE | 30 27 433 A1 | 2/1982 |
| DE | 32 18 488 A1 | 11/1983 |

(Continued)

OTHER PUBLICATIONS

Alvarez et al.; "The influence of single-pulse and tandem shock waves on bacteria", Shock Waves, vol. 17, No. 6, pp. 441-447, 2008 (Year: 2008).*

(Continued)

*Primary Examiner* — Lisa M Caputo
*Assistant Examiner* — Rose M Miller
(74) *Attorney, Agent, or Firm* — FloDesign Sonics, Inc.

(57) ABSTRACT

An apparatus for separating particles from a fluid stream includes a flow chamber that has at least one inlet and at least one outlet. At least one ultrasonic transducer is located on a wall of the flow chamber. The transducer includes a piezoelectric array with at least two piezoelectric elements. The piezoelectric array includes a piezoelectric material to create a multi-dimensional acoustic standing wave in the flow chamber. A reflector is located on the wall on the opposite side of the flow chamber from the at least one ultrasonic transducer.

18 Claims, 23 Drawing Sheets

Related U.S. Application Data is a continuation-in-part of application No. 14/026,413, filed on Sep. 13, 2013, now Pat. No. 9,458,450, which is a continuation-in-part of application No. 13/844,754, filed on Mar. 15, 2013, now Pat. No. 10,040,011.

(60) Provisional application No. 61/990,168, filed on May 8, 2014, provisional application No. 61/611,159, filed on Mar. 15, 2012, provisional application No. 61/611,240, filed on Mar. 15, 2012, provisional application No. 61/708,641, filed on Oct. 2, 2012, provisional application No. 61/754,792, filed on Jan. 21, 2013.

(51) Int. Cl.
*H01L 41/047* (2006.01)
*H01L 41/09* (2006.01)
*C12M 1/00* (2006.01)
*H01L 41/053* (2006.01)

(58) Field of Classification Search
CPC ... G01N 2015/1413; G01N 2015/1081; G01N 2015/1087; G01N 2015/1093; G01N 2001/4077; B06B 1/0622; B01D 43/00; C12M 47/02; H01L 41/047; H01L 41/0533; H01L 41/09
USPC .......................................... 73/570.5, 61.75
See application file for complete search history.

(56) References Cited

U.S. PATENT DOCUMENTS

| | | | |
|---|---|---|---|
| 3,372,370 A | 3/1968 | Cyr | |
| 3,555,311 A | 1/1971 | Weber | |
| 4,055,491 A | 10/1977 | Porath-Furedi | |
| 4,065,875 A | 1/1978 | Srna | |
| 4,118,649 A | 10/1978 | Schwartzman et al. | |
| 4,158,629 A | 6/1979 | Sawyer | |
| 4,165,273 A | 8/1979 | Azarov et al. | |
| 4,173,725 A | 11/1979 | Asai et al. | |
| 4,204,096 A | 5/1980 | Barcus et al. | |
| 4,211,949 A * | 7/1980 | Brisken | G10K 11/02 310/322 |
| 4,254,661 A | 3/1981 | Kossoff et al. | |
| 4,320,659 A | 3/1982 | Lynnworth et al. | |
| 4,344,448 A | 8/1982 | Potts | |
| 4,398,325 A | 8/1983 | Piaget et al. | |
| 4,552,669 A | 11/1985 | Sekellick | |
| 4,666,595 A | 5/1987 | Graham | |
| 4,673,512 A | 6/1987 | Schram | |
| 4,699,588 A | 10/1987 | Zinn et al. | |
| 4,743,361 A | 5/1988 | Schram | |
| 4,759,775 A | 7/1988 | Peterson et al. | |
| 4,800,316 A | 1/1989 | Wang | |
| 4,821,838 A | 4/1989 | Chen | |
| 4,836,684 A | 6/1989 | Javorik et al. | |
| 4,860,993 A | 8/1989 | Goode | |
| 4,877,516 A * | 10/1989 | Schram | B01D 21/283 209/155 |
| 4,878,210 A | 10/1989 | Mitome | |
| 4,983,189 A | 1/1991 | Peterson et al. | |
| 5,006,266 A * | 4/1991 | Schram | B01D 21/283 209/1 |
| 5,059,811 A | 10/1991 | King et al. | |
| 5,062,965 A | 11/1991 | Bernou et al. | |
| 5,085,783 A | 2/1992 | Feke et al. | |
| 5,164,094 A | 11/1992 | Stuckart | |
| 5,225,089 A | 7/1993 | Benes et al. | |
| 5,371,729 A | 12/1994 | Manna | |
| 5,395,592 A | 3/1995 | Bolleman et al. | |
| 5,431,817 A | 7/1995 | Braatz et al. | |
| 5,443,985 A | 8/1995 | Lu et al. | |
| 5,452,267 A | 9/1995 | Spevak | |
| 5,475,486 A | 12/1995 | Paoli | |
| 5,484,537 A | 1/1996 | Whitworth | |
| 5,527,460 A | 6/1996 | Trampler et al. | |
| 5,560,362 A | 10/1996 | Sliwa, Jr. et al. | |
| 5,594,165 A | 1/1997 | Madanshetty | |
| 5,604,301 A | 2/1997 | Mountford et al. | |
| 5,626,767 A | 5/1997 | Trampler et al. | |
| 5,688,405 A | 11/1997 | Dickinson et al. | |
| 5,711,888 A | 1/1998 | Trampler et al. | |
| 5,831,166 A | 11/1998 | Kozuka et al. | |
| 5,834,871 A | 11/1998 | Puskas | |
| 5,866,815 A * | 2/1999 | Schwald | B06B 1/0674 73/290 V |
| 5,902,489 A | 5/1999 | Yasuda et al. | |
| 5,912,182 A | 6/1999 | Coakley et al. | |
| 5,947,299 A | 9/1999 | Vazquez et al. | |
| 5,951,456 A | 9/1999 | Scott | |
| 6,029,518 A * | 2/2000 | Oeftering | B01D 17/041 210/748.02 |
| 6,090,295 A | 6/2000 | Raghavarao et al. | |
| 6,166,231 A | 12/2000 | Hoeksema | |
| 6,216,538 B1 * | 4/2001 | Yasuda | B01D 21/283 210/748.05 |
| 6,205,848 B1 | 6/2001 | Faber et al. | |
| 6,273,262 B1 | 8/2001 | Yasuda et al. | |
| 6,332,541 B1 | 12/2001 | Coakley et al. | |
| 6,391,653 B1 | 5/2002 | Letcher et al. | |
| 6,475,151 B2 | 11/2002 | Koger et al. | |
| 6,482,327 B1 | 11/2002 | Mori et al. | |
| 6,487,095 B1 | 11/2002 | Malik et al. | |
| 6,592,821 B1 | 7/2003 | Wada et al. | |
| 6,641,708 B1 | 11/2003 | Becker et al. | |
| 6,649,069 B2 | 11/2003 | DeAngelis | |
| 6,699,711 B1 | 3/2004 | Hahn et al. | |
| 6,727,451 B1 | 4/2004 | Fuhr et al. | |
| 6,763,722 B2 | 7/2004 | Fjield et al. | |
| 6,881,314 B1 | 4/2005 | Wang et al. | |
| 6,929,750 B2 | 8/2005 | Laurell et al. | |
| 6,936,151 B1 | 8/2005 | Lock et al. | |
| 7,008,540 B1 | 3/2006 | Weavers et al. | |
| 7,010,979 B2 | 3/2006 | Scott | |
| 7,061,163 B2 | 6/2006 | Nagahara et al. | |
| 7,081,192 B1 | 7/2006 | Wang et al. | |
| 7,093,482 B2 | 8/2006 | Berndt | |
| 7,108,137 B2 | 9/2006 | Lal et al. | |
| 7,150,779 B2 | 12/2006 | Meegan, Jr. | |
| 7,186,502 B2 | 3/2007 | Vesey | |
| 7,191,787 B1 | 3/2007 | Redeker et al. | |
| 7,322,431 B2 | 1/2008 | Ratcliff | |
| 7,331,233 B2 | 2/2008 | Scott | |
| 7,340,957 B2 | 3/2008 | Kaduchak et al. | |
| 7,373,805 B2 | 5/2008 | Hawkes et al. | |
| 7,541,166 B2 | 6/2009 | Belgrader et al. | |
| 7,601,267 B2 | 10/2009 | Haake et al. | |
| 7,673,516 B2 | 3/2010 | Janssen et al. | |
| 7,837,040 B2 | 11/2010 | Ward et al. | |
| 7,846,382 B2 | 12/2010 | Strand et al. | |
| 7,968,049 B2 | 6/2011 | Takahashi et al. | |
| 8,075,786 B2 | 12/2011 | Bagajewicz | |
| 8,080,202 B2 | 12/2011 | Takahashi et al. | |
| 8,134,705 B2 | 3/2012 | Kaduchak et al. | |
| 8,256,076 B1 | 9/2012 | Feller | |
| 8,266,950 B2 | 9/2012 | Kaduchak et al. | |
| 8,273,253 B2 | 9/2012 | Curran | |
| 8,273,302 B2 | 9/2012 | Takahashi et al. | |
| 8,309,408 B2 | 11/2012 | Ward et al. | |
| 8,319,398 B2 | 11/2012 | Vivek et al. | |
| 8,334,133 B2 | 12/2012 | Fedorov et al. | |
| 8,387,803 B2 | 3/2013 | Thorslund et al. | |
| 8,592,204 B2 | 11/2013 | Lipkens et al. | |
| 8,679,338 B2 | 3/2014 | Rietman et al. | |
| 8,691,145 B2 | 4/2014 | Dionne et al. | |
| 8,873,051 B2 | 10/2014 | Kaduchak et al. | |
| 8,889,388 B2 | 11/2014 | Wang et al. | |
| 9,272,234 B2 | 3/2016 | Lipkens et al. | |
| 9,357,293 B2 | 5/2016 | Claussen | |
| 9,365,815 B2 | 6/2016 | Miyazaki et al. | |
| 9,368,110 B1 | 6/2016 | Hershey et al. | |

(56) References Cited

U.S. PATENT DOCUMENTS

| | | | |
|---|---|---|---|
| 9,388,363 B2 | 7/2016 | Goodson et al. | |
| 9,391,542 B2 | 7/2016 | Wischnewskiy | |
| 9,403,114 B2 | 8/2016 | Kusuura | |
| 9,410,256 B2 | 8/2016 | Dionne et al. | |
| 9,416,344 B2 | 8/2016 | Lipkens et al. | |
| 9,421,553 B2 | 8/2016 | Dionne et al. | |
| 9,422,328 B2 | 8/2016 | Kennedy, III et al. | |
| 9,457,139 B2 | 10/2016 | Ward et al. | |
| 9,457,302 B2 * | 10/2016 | Lipkens | B01D 43/00 |
| 9,458,450 B2 * | 10/2016 | Lipkens | C12M 47/02 |
| 9,464,303 B2 | 10/2016 | Burke | |
| 9,476,855 B2 | 10/2016 | Ward et al. | |
| 9,480,375 B2 | 11/2016 | Marshall et al. | |
| 9,480,935 B2 | 11/2016 | Mariella, Jr. et al. | |
| 9,488,621 B2 | 11/2016 | Kaduchak et al. | |
| 9,504,780 B2 | 11/2016 | Spain et al. | |
| 9,512,395 B2 | 12/2016 | Lipkens et al. | |
| 9,513,205 B2 | 12/2016 | Yu et al. | |
| 9,514,924 B2 | 12/2016 | Morris et al. | |
| 9,517,474 B2 | 12/2016 | Mao et al. | |
| 9,675,902 B2 * | 6/2017 | Lipkens | B01D 43/00 |
| 9,701,955 B2 * | 7/2017 | Lipkens | H01L 41/1876 |
| 10,724,029 B2 * | 7/2020 | Lipkens | H01L 41/0913 |
| 2002/0038662 A1 | 4/2002 | Schuler et al. | |
| 2002/0134734 A1 | 9/2002 | Campbell et al. | |
| 2003/0015035 A1 | 1/2003 | Kaduchak et al. | |
| 2003/0028108 A1 | 2/2003 | Miller et al. | |
| 2003/0195496 A1 | 10/2003 | Maguire | |
| 2003/0209500 A1 | 11/2003 | Kock et al. | |
| 2003/0230535 A1 | 12/2003 | Affeld et al. | |
| 2004/0016699 A1 | 1/2004 | Bayevsky | |
| 2004/0035208 A1 | 2/2004 | Diaz et al. | |
| 2004/0112841 A1 | 6/2004 | Scott | |
| 2004/0124155 A1 | 7/2004 | Meegan, Jr. | |
| 2004/0149039 A1 | 8/2004 | Cardelius | |
| 2005/0031499 A1 | 2/2005 | Meier | |
| 2005/0121269 A1 | 6/2005 | Namduri | |
| 2005/0145567 A1 | 7/2005 | Quintel et al. | |
| 2005/0196725 A1 | 9/2005 | Fu | |
| 2006/0037915 A1 | 2/2006 | Strand et al. | |
| 2006/0037916 A1 | 2/2006 | Trampler | |
| 2006/0050615 A1 | 3/2006 | Swisher | |
| 2007/0053795 A1 | 3/2007 | Laugharn, Jr. et al. | |
| 2007/0224676 A1 | 9/2007 | Haq | |
| 2007/0267351 A1 | 11/2007 | Roach et al. | |
| 2007/0272618 A1 | 11/2007 | Gou et al. | |
| 2007/0284299 A1 | 12/2007 | Xu et al. | |
| 2008/0011693 A1 | 1/2008 | Li et al. | |
| 2008/0067128 A1 | 3/2008 | Hoyos et al. | |
| 2008/0105625 A1 | 5/2008 | Rosenberg et al. | |
| 2008/0181838 A1 | 7/2008 | Kluck | |
| 2008/0217259 A1 | 9/2008 | Siversson | |
| 2008/0245709 A1 | 10/2008 | Kaduchak et al. | |
| 2008/0245745 A1 | 10/2008 | Ward et al. | |
| 2008/0264716 A1 | 10/2008 | Kuiper et al. | |
| 2008/0272034 A1 | 11/2008 | Ferren et al. | |
| 2008/0272065 A1 | 11/2008 | Johnson | |
| 2008/0316866 A1 | 12/2008 | Goodemote et al. | |
| 2009/0029870 A1 | 1/2009 | Ward et al. | |
| 2009/0053686 A1 | 2/2009 | Ward et al. | |
| 2009/0087492 A1 | 4/2009 | Johnson et al. | |
| 2009/0098027 A1 | 4/2009 | Tabata et al. | |
| 2009/0104594 A1 | 4/2009 | Webb | |
| 2009/0126481 A1 | 5/2009 | Burris | |
| 2009/0178716 A1 | 7/2009 | Kaduchak et al. | |
| 2009/0194420 A1 | 8/2009 | Mariella, Jr. et al. | |
| 2009/0227042 A1 | 9/2009 | Gauer et al. | |
| 2009/0045107 A1 | 12/2009 | Ward et al. | |
| 2009/0295505 A1 | 12/2009 | Mohammadi et al. | |
| 2010/0000945 A1 | 1/2010 | Gavalas | |
| 2010/0078323 A1 | 4/2010 | Takahashi et al. | |
| 2010/0078384 A1 | 4/2010 | Yang | |
| 2010/0124142 A1 | 5/2010 | Laugharn et al. | |
| 2010/0139377 A1 | 6/2010 | Huang et al. | |
| 2010/0192693 A1 | 8/2010 | Mudge et al. | |
| 2010/0193407 A1 | 8/2010 | Steinberg et al. | |
| 2010/0206818 A1 | 8/2010 | Leong et al. | |
| 2010/0255573 A1 | 10/2010 | Bond et al. | |
| 2010/0261918 A1 | 10/2010 | Chianelli et al. | |
| 2010/0317088 A1 | 12/2010 | Radaelli et al. | |
| 2010/0323342 A1 | 12/2010 | Gonzalez Gomez et al. | |
| 2010/0330633 A1 | 12/2010 | Walther et al. | |
| 2011/0003350 A1 | 1/2011 | Schafran et al. | |
| 2011/0024335 A1 | 2/2011 | Ward et al. | |
| 2011/0092726 A1 | 4/2011 | Clarke | |
| 2011/0095225 A1 | 4/2011 | Eckelberry et al. | |
| 2011/0123392 A1 | 5/2011 | Dionne et al. | |
| 2011/0125024 A1 | 5/2011 | Mueller | |
| 2011/0146678 A1 | 6/2011 | Ruecroft et al. | |
| 2011/0154890 A1 | 6/2011 | Holm et al. | |
| 2011/0166551 A1 | 7/2011 | Schafer | |
| 2011/0189732 A1 | 8/2011 | Weinand et al. | |
| 2011/0245750 A1 | 10/2011 | Lynch et al. | |
| 2011/0262990 A1 | 10/2011 | Wang et al. | |
| 2011/0278218 A1 | 11/2011 | Dionne et al. | |
| 2011/0281319 A1 | 11/2011 | Swayze et al. | |
| 2011/0309020 A1 | 12/2011 | Rietman et al. | |
| 2012/0088295 A1 | 4/2012 | Yasuda et al. | |
| 2012/0145633 A1 | 6/2012 | Polizzotti et al. | |
| 2012/0163126 A1 | 6/2012 | Campbell et al. | |
| 2012/0175012 A1 | 7/2012 | Goodwin et al. | |
| 2012/0231504 A1 | 9/2012 | Niazi | |
| 2012/0267288 A1 | 10/2012 | Chen et al. | |
| 2012/0325727 A1 | 12/2012 | Dionne et al. | |
| 2012/0325747 A1 | 12/2012 | Reitman et al. | |
| 2012/0328477 A1 | 12/2012 | Dionne et al. | |
| 2012/0329122 A1 | 12/2012 | Lipkens et al. | |
| 2013/0017577 A1 | 1/2013 | Arunakumari et al. | |
| 2013/0115664 A1 | 5/2013 | Khanna et al. | |
| 2013/0175226 A1 | 7/2013 | Coussios et al. | |
| 2013/0217113 A1 | 8/2013 | Srinivasan et al. | |
| 2013/0277316 A1 | 10/2013 | Dutra et al. | |
| 2013/0277317 A1 | 10/2013 | LoRicco et al. | |
| 2013/0284271 A1 | 10/2013 | Lipkens et al. | |
| 2014/0011240 A1 | 1/2014 | Lipkens et al. | |
| 2014/0017758 A1 | 1/2014 | Kniep et al. | |
| 2014/0102947 A1 | 4/2014 | Baym et al. | |
| 2014/0141413 A1 | 5/2014 | Laugham, Jr. et al. | |
| 2014/0319077 A1 | 10/2014 | Lipkens et al. | |
| 2014/0377834 A1 | 12/2014 | Presz, Jr. et al. | |
| 2015/0053561 A1 | 2/2015 | Ward et al. | |
| 2015/0060581 A1 | 3/2015 | Santos et al. | |
| 2015/0321129 A1 | 11/2015 | Lipkens et al. | |
| 2016/0121331 A1 | 5/2016 | Kapur et al. | |
| 2016/0123858 A1 | 5/2016 | Kapur et al. | |
| 2016/0145563 A1 | 5/2016 | Berteau et al. | |
| 2016/0153249 A1 | 6/2016 | Mitri | |
| 2016/0175198 A1 | 6/2016 | Warner et al. | |
| 2016/0184790 A1 | 6/2016 | Sinha et al. | |
| 2016/0202237 A1 | 7/2016 | Zeng et al. | |
| 2016/0208213 A1 | 7/2016 | Doyle et al. | |
| 2016/0230168 A1 | 8/2016 | Kaduchak et al. | |
| 2016/0237110 A1 | 8/2016 | Gilmanshin et al. | |
| 2016/0237394 A1 | 8/2016 | Lipkens et al. | |
| 2016/0237395 A1 | 8/2016 | Lipkens et al. | |
| 2016/0252445 A1 | 9/2016 | Yu et al. | |
| 2016/0279540 A1 | 9/2016 | Presz, Jr. et al. | |
| 2016/0279551 A1 | 9/2016 | Foucault | |
| 2016/0312168 A1 | 10/2016 | Pizzi | |
| 2016/0314868 A1 | 10/2016 | El-Zahab et al. | |
| 2016/0319270 A1 | 11/2016 | Lipkens et al. | |
| 2016/0325206 A1 | 11/2016 | Presz, Jr. et al. | |
| 2016/0332159 A1 | 11/2016 | Dual et al. | |
| 2016/0339360 A1 | 11/2016 | Lipkens et al. | |
| 2016/0347628 A1 | 12/2016 | Dionne et al. | |
| 2016/0355776 A1 | 12/2016 | Lipkens et al. | |
| 2016/0361670 A1 | 12/2016 | Lipkens et al. | |
| 2016/0363579 A1 | 12/2016 | Lipkens et al. | |

FOREIGN PATENT DOCUMENTS

| | | |
|---|---|---|
| DE | 196 48 519 A1 | 6/1998 |
| DE | 103 19 467 B3 | 7/2004 |
| DE | 10 2008 006 501 A1 | 9/2008 |

(56) References Cited

FOREIGN PATENT DOCUMENTS

| | | |
|---|---|---|
| EP | 0 641 606 | 3/1995 |
| EP | 1 175 931 A1 | 1/2002 |
| EP | 1 254 669 B1 | 11/2002 |
| GB | 2 420 510 A | 5/2006 |
| JP | 9-136090 | 5/1997 |
| RU | 2085933 | 7/1997 |
| SU | 629496 | 10/1978 |
| WO | WO 87/07178 A1 | 12/1987 |
| WO | WO 89/11899 A1 | 12/1989 |
| WO | WO 90/05008 | 3/1990 |
| WO | WO 97/34643 | 9/1997 |
| WO | WO 98/017373 | 4/1998 |
| WO | WO 98/50133 A1 | 11/1998 |
| WO | WO 02/072234 A1 | 9/2002 |
| WO | WO 03/089567 | 10/2003 |
| WO | WO 2004/079716 A1 | 9/2004 |
| WO | WO 2009/063198 | 5/2009 |
| WO | WO 2009/111276 A1 | 9/2009 |
| WO | WO 2009/144709 A1 | 12/2009 |
| WO | WO 2010/024753 A1 | 4/2010 |
| WO | WO 2010/040394 A1 | 4/2010 |
| WO | WO 2011/023949 A2 | 3/2011 |
| WO | WO 2011/025890 A1 | 3/2011 |
| WO | WO 2011/027146 A2 | 3/2011 |
| WO | WO 2011/161463 A2 | 12/2011 |
| WO | WO 2013/043297 A1 | 3/2013 |
| WO | WO 2013/055517 A1 | 4/2013 |
| WO | WO 2013/138797 A1 | 9/2013 |
| WO | WO 2013/148376 | 10/2013 |
| WO | WO 2013/159014 A1 | 10/2013 |
| WO | WO 2014/014941 A1 | 1/2014 |
| WO | WO 2014/029505 | 2/2014 |
| WO | WO 2014/055219 A2 | 4/2014 |
| WO | WO 2014/124306 A1 | 8/2014 |
| WO | WO 2014/153651 | 10/2014 |
| WO | WO 2015/006730 | 1/2015 |

OTHER PUBLICATIONS

Cravatto et al.; "Improved extraction of vegetable oils under high-intensity ultrasound and/or microwaves", Ultrasonics Sonochemistry, vol. 15, No. 5, pp. 898-902 (Year: 2008).*

Seymour et al., "Piezoelectric Polymers", J. Chem Edu, 1990, 67(9), p. 763, Sep. 1990 (Year: 1990).*

Annex to Form PCT/ISA/206—PCT/US2013/037475, Communication to the Results of the Partial International Search Report, dated Jul. 18, 2013 (Year: 2013).*

Ponge et al.; "Numerical and experimental characterization of pre-fractal anisotropic stacks", Proceedings of the Acoustics 2012 Nantes Conference, Apr. 23-27, 2012, Nantes France, pp. 277-282 (Year: 2012).*

Benes et al.; Ultrasonic Separation of Suspended Particles, 2001 IEEE Ultrasonics Symposium; Oct. 7-10, 2001; pp. 649-659; Atlanta, Georgia.

Castilho et al.; Animal Cell Technology: From Biopharmaceuticals to Gene Therapy; 11—Animal Cell Separation; 2008.

Castro; Tunable gap and quantum quench dynamics in bilayer graphene; Jul. 13, 2010; Mathematica Summer School.

Garcia-Lopez, et al; Enhanced Acoustic Separation of Oil-Water Emulsion in Resonant Cavities. The Open Acoustics Journal. 2008, vol. 1, pp. 66-71.

Hill et al.; Ultrasonic Particle Manipulation; Microfluidic Technologies for Miniaturized Analysis Systems, Jan. 2007, pp. 359-378.

Ilinskii et al.; Acoustic Radiation Force on a Sphere in Tissue; AIP Conference Proceedings; 2012.

Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.

Latt et al.; Ultrasound-membrane hybrid processes for enhancement of filtration properties; Ultrasonics sonochemistry 13.4 (2006): 321-328.

Li et al.; Electromechanical behavior of PZT-brass unimorphs; J. Am. Ceram. Soc. vol. 82; No. 7; pp. 1733-1740, 1999.

Lipkens et al.; Frequency sweeping and fluid flow effects on particle trajectories in ultrasonic standing waves; Acoustics 08, Paris, Jun. 29-Jul. 4, 2008.

Lipkens et al.; Prediction and measurement of particle velocities in ultrasonic standing waves; J. Acoust. Soc. Am., 124 No. 4, pp. 2492 (A) 2008.

Lipkens et al.; Separation of micron-sized particles in macro-scale cavities by ultrasonic standing waves; Presented at the International Congress on Ultrasonics, Santiago; Jan. 11-17, 2009.

Lipkens et al.; The effect of frequency sweeping and fluid flow on particle trajectories in ultrasonic standing waves; IEEE Sensors Journal, vol. 8, No. 6, pp. 667-677, 2008.

Lipkens et al.; Separation of bacterial spores from flowering water in macro-scale cavities by ultrasonic standing waves; submitted/uploaded to arxiv.org/abs/1006.5467 on Jun. 28, 2010.

Meribout et a.; An Industrial-Prototype Acoustic Array for Real-Time Emulsion Layer Detection in Oil Storage Tanks; IEEE Sensors Journal, vol. 9, No. 12, Dec. 2009.

Nilsson et al.; Review of cell and particle trapping in microfluidic systems; Department of Measurement Technology and Industrial Electrical Engineering, Div. of Nanobiotechnology, Lund University, P.O. Box 118. Lund, Sweden, Analytica Chimica Acta 649, Jul. 14, 2009, pp. 141-157.

Pangu et al.; Droplet transport and coalescence kinetics in emulsions subjected to acoustic fields; Ultrasonics 46, pp. 289-302 (2007).

Ponomarenko et al.; Density of states and zero Landau level probed through capacitance of graphene; Nature Nanotechnology Letters, Jul. 5, 2009; DOI: 10.1038/NNAN0.2009.177.

Ryll et al.; Performance of Small-Scale CHO Perfusion Cultures Using an Acoustic Cell Filtration Device for Cell Retention: Characterization of Separation Efficiency and Impact of Perfusion on Product Quality; Biotechnology and Bioengineering; vol. 69; Iss. 4; pp. 440-449; Aug. 2000.

Volpin et al.; Mesh simplification with smooth surface reconstruction; Computer-Aided Design; vol. 30; No. 11; 1998.

Wang et al.; Retention and Viability Characteristics of Mammalian Cells in an Acoustically Driven Polymer Mesh; Biotechnol. Prog. 2004, pp. 384-387 (2004).

Wicklund et al.; Ultrasonic Manipulation of Single Cells; Methods in Molecular Biology; vol. 853; pp. 1777-196; 2012.

European Search Report of European Application No. 11769474.5, dated Sep. 5, 2013.

European Search Report of European Application No. 13760840.2, dated Feb. 4, 2016.

European Search Report of European Application No. 13721179.3 dated Feb. 23, 2016.

International Search Report and Written Opinion dated Dec. 20, 2011, for corresponding PCT application No. PCT/US2011/032181.

International Search Report and Written Opinion dated Feb. 27, 2012, for PCT application No. PCT/US2011/040787.

International Search Report and Written Opinion of International Application No. PCT/US2012/051804 dated Nov. 16, 2012.

International Search Report and Written Opinion of International Application No. PCT/US2013/037404 dated Jun. 21, 2013.

International Search Report and Written Opinion of International Application No. PCT/US2013/032705 dated Jul. 26, 2013.

International Search Report and Written Opinion of International Application No. PCT/US2013/050729 dated Sep. 25, 2013.

International Search Report dated Feb. 18, 2014 in corresponding PCT Application No. PCT/US2013/059640.

International Search Report for corresponding PCT Application Serial No. PCT/US2014/015382 dated May 6, 2014.

International Search Report for PCT/US2014/035557 dated Aug. 27, 2014.

International Search Report for PCT/US2014/043930 dated Oct. 22, 2014.

(56) References Cited

OTHER PUBLICATIONS

International Search Report for PCT/US2014/046412 dated Oct. 27, 2014.
International Search Report for PCT/US2014/064088 dated Jan. 30, 2015.
Extended European Search Report for Application No. EP 12833859.7 dated Mar. 20, 2015.
International Search Report and Written Opinion for International Application No. PCT/US2015/010595 dated Apr. 15, 2015.
International Search Report for PCT/US2015/019755 dated May 4, 2015.
International Search Report dated Jul. 30, 2015 for International Application No. PCT/US2015/030009.
International Search Report for PCT/US2015/039125 dated Sep. 30, 2015.
International Search Report and Written Opinion for PCT Application Serial No. PCT/US2015/053200 dated Dec. 28, 2015.
European Search Report of European Application No. 11796470.0 dated Jan. 5, 2016.
International Search Report and Written Opinion for International Application No. PCT/US2015/066884, dated Mar. 22, 2016.
International Search Report and Written Opinion for International Application No. PCT/US2016/024082 dated Jun. 27, 2016.
International Search Report and Written Opinion for International Application No. PCT/US2016/044586 dated Oct. 21, 2016.
International Search Report and Written Opinion for International Application No. PCT/US2016/031357 dated Jul. 26, 2016.
International Search Report and Written Opinion for International Application No. PCT/US2015/024365 dated Oct. 13, 2016.
International Search Report and Written Opinion for International Application No. PCT/US2016/041664 dated Oct. 18, 2016.
International Search Report and Written Opinion for International Application No. PCT/US2016/049088 dated Nov. 28, 2016.
International Search Report and Written Opinion for International Application No. PCT/US2016/050415 dated Nov. 28, 2016.
International Search Report and Written Opinion for International Application No. PCT/US2016/037104 dated Dec. 16, 2016.
Phys. org. "Engineers develop revolutionary nanotech water desalination membrane." Nov. 6, 2006. phys.org/news82047372.html.
Sony New Release: <www.sony.net/SonyInfo/News/Press/201010/10-137E/index.html>.

\* cited by examiner

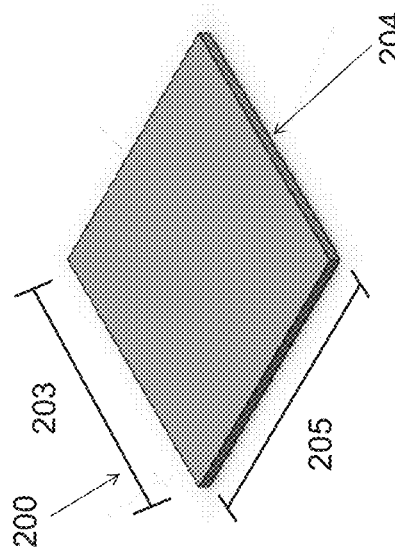
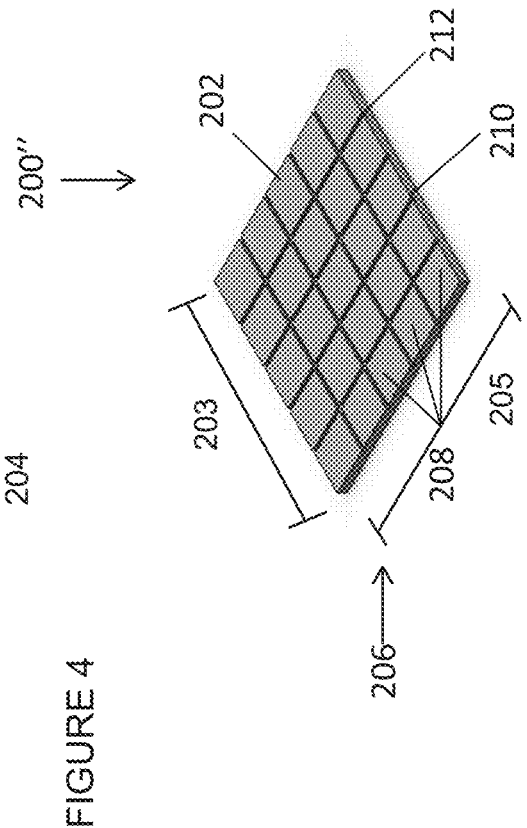
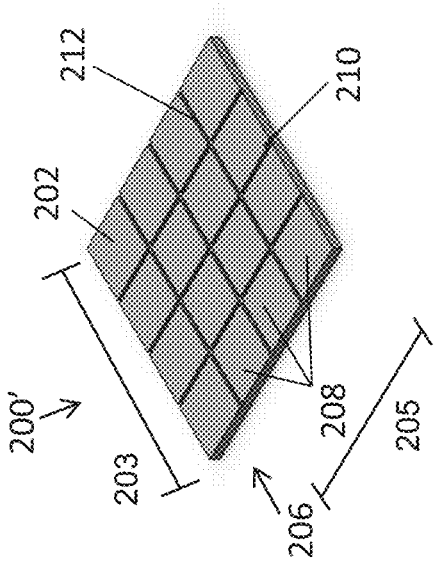
FIGURE 4
FIGURE 5
FIGURE 6

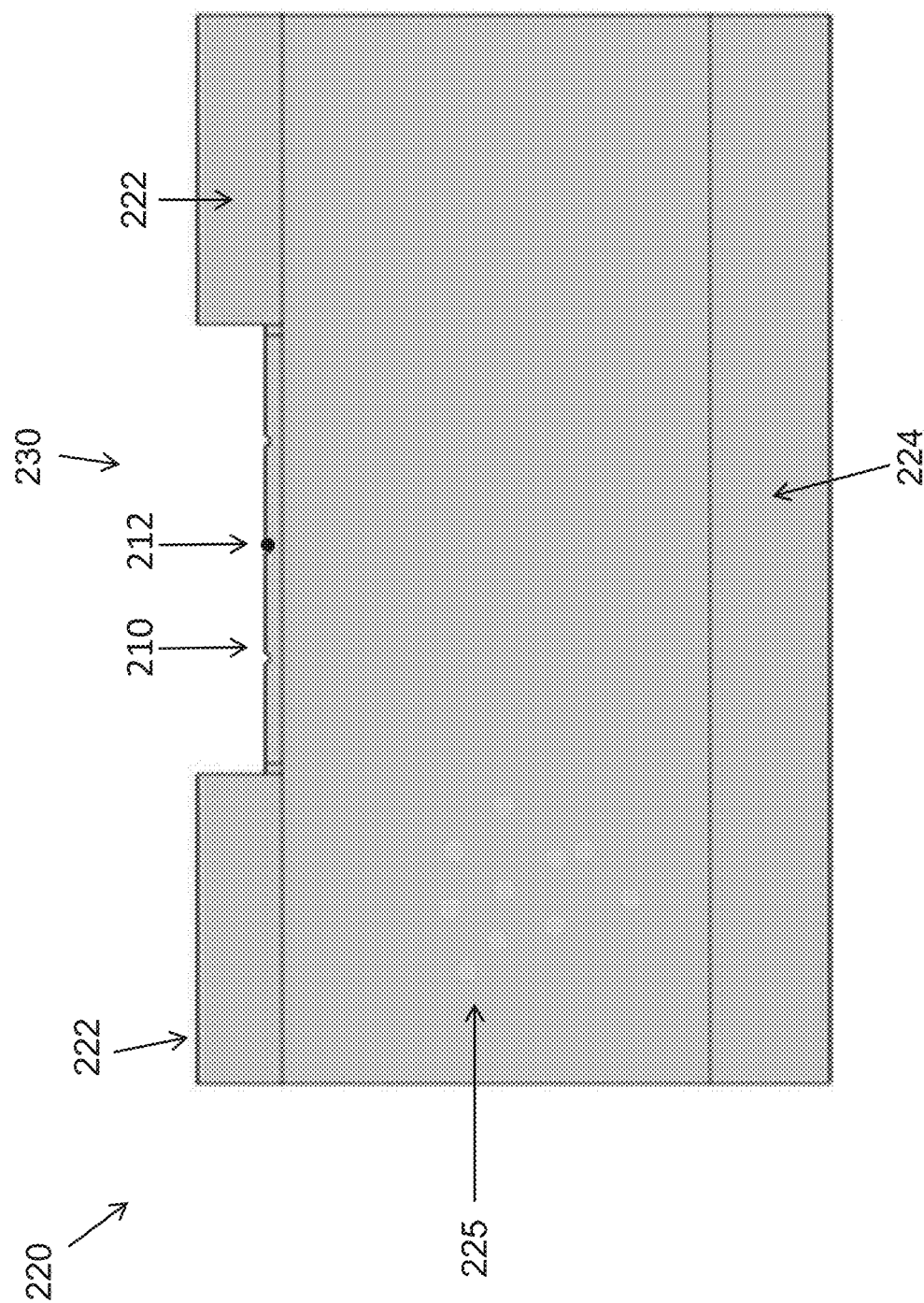

$|F_{ARF}|$ $F_{ARF}$ (Y-Component)

$F_{ARF}$ (X-Component)

Acoustic Potential, U

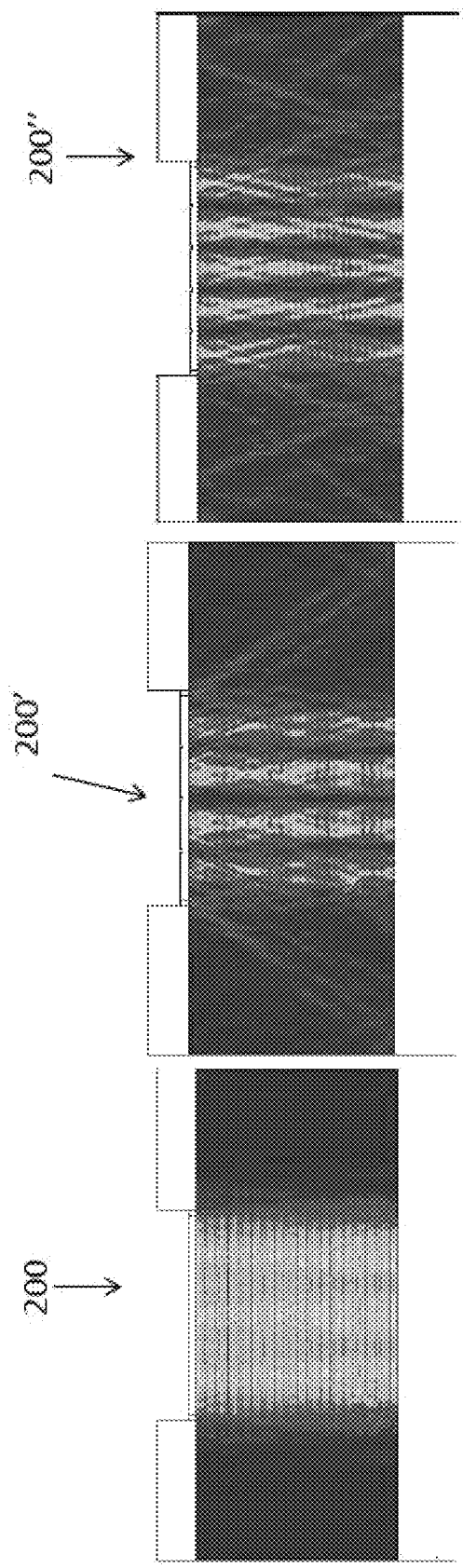

ACOUSTOPHORETIC DEVICE WITH PIEZOELECTRIC TRANSDUCER ARRAY

This application is a continuation-in-part of U.S. patent application Ser. No. 14/708,035, filed May 8, 2015, now U.S. Pat. No. 9,457,302, which claims priority to U.S. Provisional Patent Application Ser. No. 61/990,168, filed May 8, 2014, and which is also a continuation-in-part of U.S. patent application Ser. No. 14/026,413, filed Sep. 13, 2013, which is a continuation-in-part of U.S. patent application Ser. No. 13/844,754, filed Mar. 15, 2013, which claimed the benefit of U.S. Provisional Patent Application Ser. No. 61/611,159, filed Mar. 15, 2012, and of U.S. Provisional Patent Application Ser. No. 61/611,240, also filed Mar. 15, 2012, and of U.S. Provisional Patent Application Ser. No. 61/708,641, filed on Oct. 2, 2012, and of U.S. Provisional Patent Application Ser. No. 61/754,792, filed Jan. 21, 2013. These applications are incorporated herein by reference in their entireties.

BACKGROUND

The ability to separate a particle/fluid mixture into its separate components is desirable in many applications. Acoustophoresis is the separation of particles using high intensity sound waves, and without the use of membranes or physical size exclusion filters. It has been known that high intensity standing waves of sound can exert forces on particles in a fluid when there is a differential in both density and/or compressibility, otherwise known as the acoustic contrast factor. The pressure profile in a standing wave contains areas of local minimum pressure amplitudes at its nodes and local maxima at its anti-nodes. Depending on the density and compressibility of the particles, they will be trapped at the nodes or anti-nodes of the standing wave. The higher the frequency of the standing wave, the smaller the particles that can be trapped due the pressure of the standing wave.

Efficient separation technologies for multi-component liquid streams that eliminate any waste and reduce the required energy, thereby promoting a sustainable environment, are needed.

BRIEF DESCRIPTION

The present disclosure relates to systems and devices for acoustophoresis on preferably a large scale. The devices use one or more unique ultrasonic transducers as described herein. The transducer includes a piezoelectric array made from a plurality of piezoelectric elements. The transducer is driven at frequencies that produce multi-dimensional standing waves.

Disclosed in various embodiments herein are apparatuses for separating a second fluid or a particulate from a host fluid, comprising: a flow chamber having at least one inlet and at least one outlet; at least one ultrasonic transducer located on a wall of the flow chamber, the transducer including a piezoelectric array formed from a plurality of piezoelectric elements which can be driven by a voltage signal to create a multi-dimensional acoustic standing wave in the flow chamber; and at least one reflector located on the wall on the opposite side of the flow chamber from the at least one ultrasonic transducer. The axial and lateral acoustic forces are of the same order of magnitude. The second fluid or particulate agglomerates at the pressure nodes (minima of the acoustic radiation potential) of the multi-dimensional acoustic standing wave, and continuously falls out of the multi-dimensional acoustic standing wave due to gravity separation, or continuously rises out of the multi-dimensional acoustic standing wave due to buoyancy.

In some embodiments, the piezoelectric array is present on a single crystal, with one or more channels separating the piezoelectric elements from each other. A potting material different from the piezoelectric material can be present in the one or more channels. The potting material may be a polymer, such as an epoxy.

In other embodiments, each piezoelectric element is physically separated from surrounding piezoelectric elements by a potting material. The potting material may be a polymer, such as an epoxy.

The piezoelectric array can be a rectangular array. Each piezoelectric element may have the same dimensions. Each piezoelectric element may be individually connected to its own pair of electrodes.

In particular embodiments, a contoured nozzle wall is located upstream of the at least one inlet of the flow chamber.

Also disclosed are methods of separating a second fluid or a particulate from a host fluid, comprising: flowing a mixture of the host fluid and the second fluid or particulate through an apparatus, the apparatus comprising: a flow chamber having at least one inlet and at least one outlet; at least one ultrasonic transducer located on a wall of the flow chamber, the transducer including a piezoelectric array formed from a plurality of piezoelectric elements which can be driven by a voltage signal to create a multi-dimensional standing wave in the flow chamber; and at least one reflector located on the wall on the opposite side of the flow chamber from the at least one ultrasonic transducer; and sending voltage signals to the piezoelectric array to form a multi-dimensional acoustic standing wave that traps the second fluid or particulate against the flow of the fluid, permitting agglomeration such that the second fluid or particulate increases in size and continuously falls out of the multi-dimensional acoustic standing wave through gravity separation. The separated material may be swept from the chamber by the fluid flow, collected in a pocket, or compacted into a smaller volume.

The particulate may be Chinese hamster ovary (CHO) cells, NS0 hybridoma cells, baby hamster kidney (BHK) cells, or human cells; lymphocytes such as T cells (e.g., regulatory T-cells (Tregs), Jurkat T-cells), B cells, or NK cells; their precursors, such as peripheral blood mononuclear cells (PBMCs); algae or other plant cells, bacteria, viruses, or microcarriers.

Sometimes, the piezoelectric elements are operated out of phase with each other. Other times, the piezoelectric elements are operated in phase with each other The flow rate of the host fluid through the flow chamber may be at least 25 mL/min. The piezoelectric elements may be operated at a frequency in a range of 100 kHz to 20 MHz, or in more specific embodiments from about 2 MHz to about 2.5 MHz.

In most embodiments, the multi-dimensional standing wave results in an acoustic radiation force having an axial force component and a lateral force component that are of the same order of magnitude.

The piezoelectric array can be present on a single crystal, with one or more channels separating the piezoelectric elements from each other. A potting material different from the piezoelectric material may be present in the one or more channels.

In other embodiments, each piezoelectric element is physically separated from surrounding piezoelectric elements by a potting material. Each piezoelectric element may be individually connected to its own pair of electrodes.

These and other non-limiting characteristics are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

FIG. 4 is a conventional single-piece monolithic piezoelectric crystal used in an ultrasonic transducer.

FIG. 5 is an exemplary rectangular piezoelectric array having 16 piezoelectric elements used in the transducers of the present disclosure.

FIG. 6 is another exemplary rectangular piezoelectric array having 25 piezoelectric elements used in the transducers of the present disclosure.

FIG. 13 shows a schematic of a two-dimensional numerical model developed for the simulation of an ultrasonic transducer and transducer array.

FIG. 14A compares the acoustic potential U. FIG. 14B compares the x-component of the acoustic radiation force (ARF). FIG. 14C compares the y-component of the ARF. FIG. 14D compares the absolute value of the ARF.

FIG. 15 is a diagram showing the amplitude of the acoustic standing wave generated by a monolithic piezoelectric crystal in the model of FIG. 13. The frequency is at 2.245 MHz. The horizontal axis is the location along the X-axis, and the vertical axis is the location along the Y-axis between the transducer and the reflector.

FIG. 16 is a diagram showing the amplitude of the acoustic standing wave generated by the 4-element piezoelectric array in the model of FIG. 13. The frequency is at 2.245 MHz with phasing between the elements being varied.

FIG. 17 is a diagram showing the amplitude of the acoustic standing wave generated by the 5-element piezoelectric array in the model of FIG. 13. The frequency is at 2.245 MHz with phasing between the elements being varied.

DETAILED DESCRIPTION

Figure 1A:
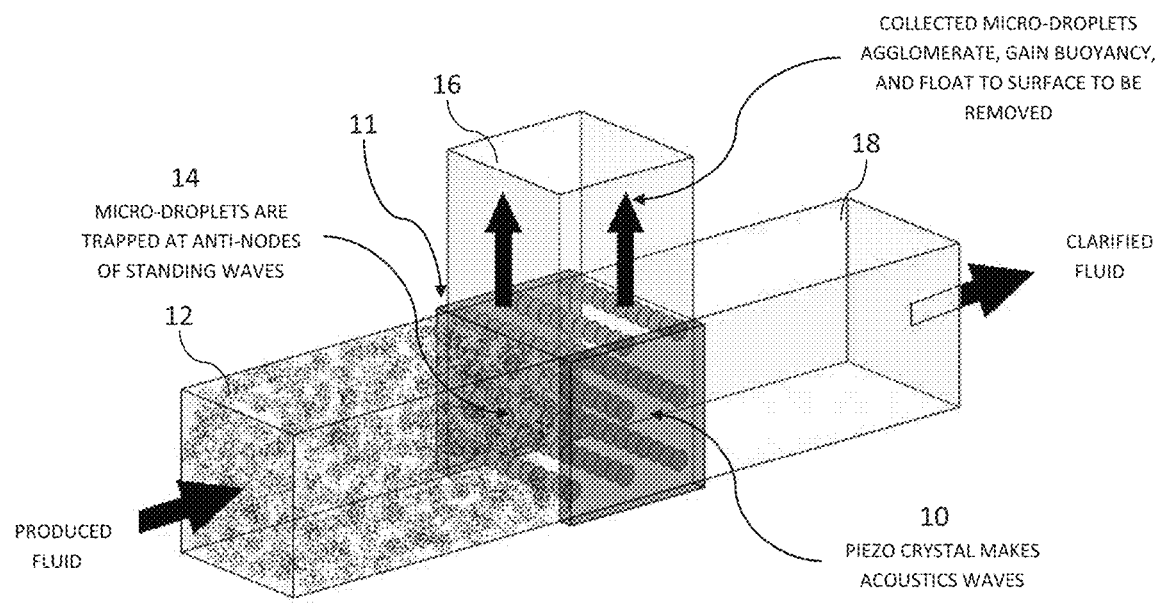
FIG. 1A is a diagram illustrating the function of an acoustophoretic separator with a secondary fluid or particles less dense than the host fluid.

The present disclosure may be understood more readily by reference to the following detailed description of desired embodiments and the examples included therein. In the following specification and the claims which follow, reference will be made to a number of terms which shall be defined to have the following meanings.

The singular forms "a," "an," and "the" include plural referents unless the context clearly dictates otherwise.

The term "comprising" is used herein as requiring the presence of the named components/steps and allowing the presence of other components/steps. The term "comprising" should be construed to include the term "consisting of", which allows the presence of only the named components/steps, along with any impurities that might result from the manufacture of the named components/steps.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

The terms "substantially" and "about" can be used to include any numerical value that can vary without changing the basic function of that value. When used with a range, "substantially" and "about" also disclose the range defined by the absolute values of the two endpoints, e.g. "about 2 to about 4" also discloses the range "from 2 to 4." The terms "substantially" and "about" may refer to plus or minus 10% of the indicated number.

It should be noted that many of the terms used herein are relative terms. For example, the terms "upper" and "lower" are relative to each other in location, i.e. an upper component is located at a higher elevation than a lower component in a given orientation, but these terms can change if the device is flipped. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, i.e. the flow fluids through an upstream component prior to flowing through the downstream component. It should be noted that in a loop, a first component can be described as being both upstream of and downstream of a second component.

The terms "horizontal" and "vertical" are used to indicate direction relative to an absolute reference, i.e. ground level. The terms "above" and "below", or "upwards" and "downwards" are also relative to an absolute reference; an upwards flow is always against the gravity of the earth.

The present application refers to "the same order of magnitude." Two numbers are of the same order of magnitude if the quotient of the larger number divided by the smaller number is a value of at least 1 and less than 10.

The acoustophoretic separation technology of the present disclosure employs ultrasonic acoustic standing waves to trap, i.e., hold stationary, particles or a secondary fluid in a host fluid stream. The particles or secondary fluid collect at the nodes or anti-nodes of the multi-dimensional acoustic standing wave, depending on the particles' or secondary fluid's acoustic contrast factor relative to the host fluid, forming clusters that eventually fall out of the multi-dimensional acoustic standing wave when the clusters have grown to a size large enough to overcome the holding force of the multi-dimensional acoustic standing wave (e.g. by coalescence or agglomeration). This is an important distinction from previous approaches where particle trajectories were merely altered by the effect of the acoustic radiation force. The scattering of the acoustic field off the particles results in a three dimensional acoustic radiation force, which acts as a three-dimensional trapping field. The acoustic radiation force is proportional to the particle volume (e.g. the cube of the radius) when the particle is small relative to the wavelength. It is proportional to frequency and the acoustic contrast factor. It also scales with acoustic energy (e.g. the square of the acoustic pressure amplitude). For harmonic excitation, the sinusoidal spatial variation of the force is what drives the particles to the stable axial positions within the standing waves. When the acoustic radiation force exerted on the particles is stronger than the combined effect of fluid drag force and buoyancy and gravitational force, the particle is trapped within the acoustic standing wave field. This results in concentration, agglomeration and/or coalescence of the trapped particles that will then continuously fall out of the multi-dimensional acoustic standing wave through gravity separation. The strong lateral forces create rapid clustering of particles. Relatively large solids of one material can thus be separated from smaller particles of a different material, the same material, and/or the host fluid through enhanced gravitational separation.

In this regard, the contrast factor is the difference between the compressibility and density of the particles and the fluid itself. These properties are characteristic of the particles and the fluid themselves. Most cell types present a higher density and lower compressibility than the medium in which they are suspended, so that the acoustic contrast factor between the cells and the medium has a positive value. As a result, the axial acoustic radiation force (ARF) drives the cells, with a positive contrast factor, to the pressure nodal planes, whereas cells or other particles with a negative contrast factor are driven to the pressure anti-nodal planes. The radial or lateral component of the acoustic radiation force trap the cells. The radial or lateral component of the ARF is larger than the combined effect of fluid drag force and gravitational force. The radial or lateral component drives the cells/particles to planes where they can cluster into larger groups, which will then gravity separate from the fluid.

As the cells agglomerate at the nodes of the standing wave, there is also a physical scrubbing of the cell culture media that occurs whereby more cells are trapped as they come in contact with the cells that are already held within the standing wave. This generally separates the cells from the cell culture media. The expressed biomolecules remain in the nutrient fluid stream (i.e. cell culture medium).

For three-dimensional acoustic fields, Gor'kov's formulation can be used to calculate the acoustic radiation force $F_{ac}$ applicable to any sound field. The primary acoustic radiation force $F_{ac}$ is defined as a function of a field potential U, $$F_A = -\nabla(U),$$

where the field potential U is defined as $$U = V_0 \left[ \frac{\langle p^2 \rangle}{2\rho_f c_f^2} f_1 - \frac{3\rho_f \langle u^2 \rangle}{4} f_2 \right],$$

and $f_1$ and $f_2$ are the monopole and dipole contributions defined by $$f_1 = 1 - \frac{1}{\Lambda \sigma^2},$$
$$f_2 = \frac{2(\Lambda - 1)}{2\Lambda + 1},$$

where p is the acoustic pressure, u is the fluid particle velocity, $\Lambda$ is the ratio of cell density $\rho_p$ to fluid density $\rho_f$, $\sigma$ is the ratio of cell sound speed $c_p$ to fluid sound speed $c_f$, $V_o$ is the volume of the cell, and $\langle \rangle$ indicates time averaging over the period of the wave. Gor'kov's formulation applies to particles smaller than the wavelength. For larger particle sizes, Ilinskii provides equations for calculating the 3D acoustic radiation forces for any particle size. See Ilinskii, *Acoustic Radiation Force on a Sphere in Tissue*, The Journal of the Acoustical Society of America, 132, 3, 1954 (2012), which is incorporated herein by reference.

Perturbation of the piezoelectric crystal in an ultrasonic transducer in a multimode fashion allows for generation of a multidimensional acoustic standing wave. A piezoelectric crystal can be specifically designed to deform in a multi-mode fashion at designed frequencies, allowing for generation of a multi-dimensional acoustic standing wave. The multi-dimensional acoustic standing wave may be generated by distinct modes of the piezoelectric crystal such as the 3×3 mode that would generate multidimensional acoustic standing waves. A multitude of multidimensional acoustic standing waves may also be generated by allowing the piezoelectric crystal to vibrate through many different mode shapes. Thus, the crystal would excite multiple modes such as a 0×0 mode (i.e. a piston mode) to a 1×1, 2×2, 1×3, 3×1, 3×3, and other higher order modes and then cycle back through the lower modes of the crystal (not necessarily in straight order). This switching or dithering of the crystal between modes allows for various multidimensional wave shapes, along with a single piston mode shape to be generated over a designated time.

In the present disclosure, a single ultrasonic transducer contains a rectangular array of piezoelectric elements, which can be operated such that some components of the array will be out of phase with other components of the array. This can also separate materials in a fluid stream.

One specific application for the acoustophoresis device is in the processing of bioreactor materials. In a fed batch bioreactor, it is important at the end of the production cycle to filter all of the cells and cell debris from the expressed materials that are in the fluid stream. The expressed materials are composed of biomolecules such as recombinant proteins or monoclonal antibodies, and are the desired product to be recovered. Through the use of acoustophoresis, the separation of the cells and cell debris is very efficient and leads to very little loss of the expressed materials. This is an improvement over the current filtration processes (depth filtration, tangential flow filtration, centrifugation), which show limited efficiencies at high cell densities, so that the loss of the expressed materials in the filter beds themselves can be up to 5% of the materials produced by the bioreactor. The use of mammalian cell cultures including Chinese hamster ovary (CHO), NS0 hybridoma cells, baby hamster kidney (BHK) cells, and human cells has proven to be a very efficacious way of producing/expressing the recombinant proteins and monoclonal antibodies required of today's pharmaceuticals. The filtration of the mammalian cells and the mammalian cell debris through acoustophoresis aids in greatly increasing the yield of the fed batch bioreactor. The acoustophoresis process, through the use of multidimensional acoustic waves, may also be coupled with a standard filtration process upstream or downstream, such as depth filtration using diatomaceous earth, tangential flow filtration (TFF), or other physical filtration processes.

Another type of bioreactor, a perfusion reactor, uses continuous expression of the target protein or monoclonal antibodies from the CHO cells. This enables a much smaller footprint in faster production cycle. The use of acoustophoresis to hold the CHO cells in a fluid stream as they are producing/expressing the proteins is a very efficient and closed loop way of production. It also allows for a maximum production efficiency of the proteins and monoclonal antibodies in that none of the materials are lost in a filter bed.

In the fed batch bioreactor process, the acoustophoresis device uses singular or multiple standing waves to trap the cells and cell debris. The cells and cell debris, having a positive contrast factor, move to the nodes (as opposed to the anti-nodes) of the standing wave. As the cells and cell debris agglomerate at the nodes of the standing wave, there is also a physical scrubbing of the fluid stream that occurs whereby more cells are trapped as they come in contact with the cells that are already held within the standing wave. When the cells in the multi-dimensional acoustic standing wave agglomerate to the extent where the mass is no longer able to be held by the acoustic wave, the aggregated cells and cell debris that have been trapped fall out of the fluid stream through gravity, and can be collected separately. This is a continuous process of gravitational separation.

Advanced multi-physics and multiple length scale computer models and high frequency (MHz), high-power, and high-efficiency ultrasonic drivers with embedded controls have been combined to arrive at new designs of acoustic resonators driven by arrays of piezoelectric transducers, resulting in acoustophoretic separation devices that far surpass current capabilities.

Desirably, such transducers generate a multi-dimensional acoustic standing wave in the fluid that exerts a lateral force on the suspended particles/secondary fluid to accompany the axial force so as to increase the particle trapping capabilities of a acoustophoretic system. Typical results published in literature state that the lateral force is two orders of magnitude smaller than the axial force. In contrast, the technology disclosed in this application provides for a lateral force to be of the same order of magnitude as the axial force.

The system is driven by a control signal and amplifier (not shown). The system performance is monitored and controlled by a computer. It may be necessary, at times, due to acoustic streaming, to modulate the frequency or voltage amplitude of the standing wave. This may be done by amplitude modulation and/or by frequency modulation. The duty cycle of the propagation of the standing wave may also be utilized to achieve certain results for trapping of materials. In other words, the acoustic beam may be turned on and shut off at different frequencies to achieve desired results.

The lateral force of the total acoustic radiation force (ARF) generated by the ultrasonic transducers of the present disclosure is significant and is sufficient to overcome the fluid drag force at high linear velocities up to 2 cm/s and beyond. For example, linear velocities through the devices of the present disclosure can be a minimum of 4 cm/min for separation of cells/particles, and can be as high as 2 cm/sec for separation of oil/water phases. Flow rates can be a minimum of 25 mL/min, and can range as high as 40 mL/min to 1000 mL/min, or even higher. This is true for batch reactors, fed-batch bioreactors and perfusion bioreactors.

A diagrammatic representation of an embodiment for removing oil or other lighter-than-water material is shown in FIG. 1A. Excitation frequencies typically in the range from hundreds of kHz to 10s of MHz are applied by transducer 10. One or more standing waves are created between the transducer 10 and the reflector 11. Microdroplets 12 are trapped in standing waves at the pressure anti-nodes 14 where they agglomerate, aggregate, clump, or coalesce, and, in the case of buoyant material, float to the surface and are discharged via an effluent outlet 16 located above the flow path. Clarified water is discharged at outlet 18. The acoustophoretic separation technology can accomplish multi-component particle separation without any fouling at a much reduced cost.

Figure 1B:
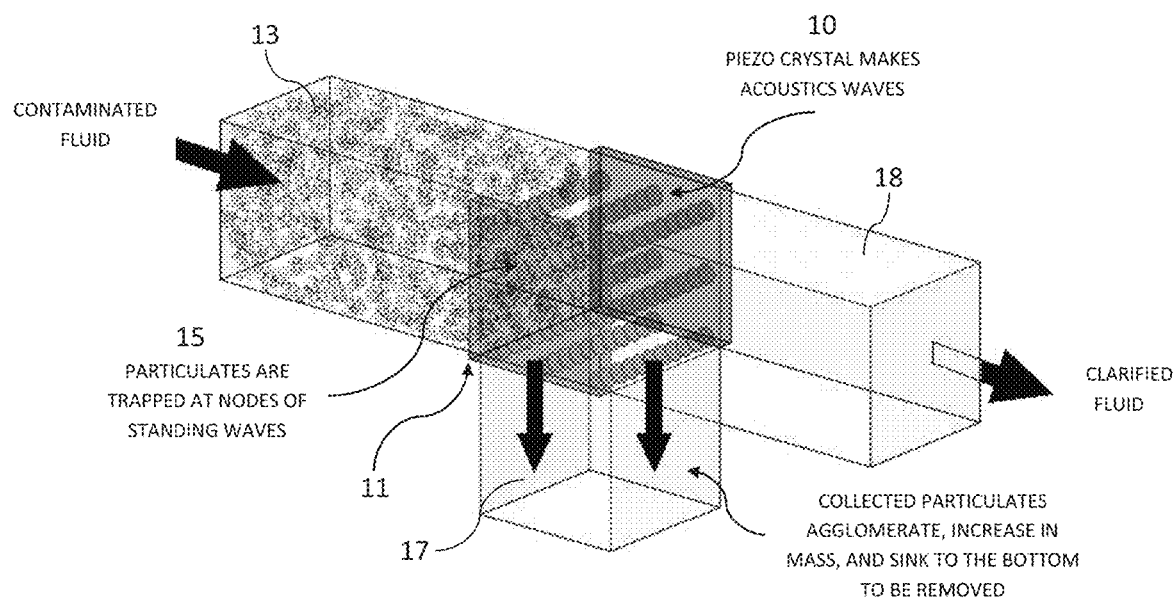
FIG. 1B is a diagram illustrating the function of an acoustophoretic separator with a secondary fluid or particles denser than the host fluid.

A diagrammatic representation of an embodiment for removing contaminants or other heavier-than-water material is shown in FIG. 1B. Excitation frequencies typically in the range from hundreds of kHz to 10s of MHz are applied by transducer 10. Contaminants in the incoming water 13 are trapped in standing waves at the pressure nodes 15 where they agglomerate, aggregate, clump, or coalesce, and, in the case of heavier material, sink to the bottom collector and are discharged via an effluent outlet 17 located below the flow path. Clarified water is discharged at outlet 18.

Generally, the transducers are arranged so that they cover the entire cross-section of the flow path. The acoustophoretic separation system of FIG. 1A or FIG. 1B has, in certain embodiments, a square cross section of 6.375 inches×6.375 inches which operates at flow rates of up to 5 gallons per minute (GPM), or a linear velocity of 12.5 mm/sec. The transducers 10 are PZT-8 (Lead Zirconate Titanate) transducers with a 1 inch×1 inch square cross section and a nominal 2 or 3 MHz resonance frequency. Each transducer consumes about 60 W of power for droplet trapping at a flow rate of 5 GPM. This translates in an energy cost of 0.500 kW hr/m$^3$. This is an indication of the very low cost of energy of this technology. Desirably, each transducer is powered and controlled by its own amplifier. One application for this embodiment is to shift the particle size distribution through agglomeration, aggregation, clumping or coalescing of the micron-sized oil droplets into much larger droplets.

Figure 2:
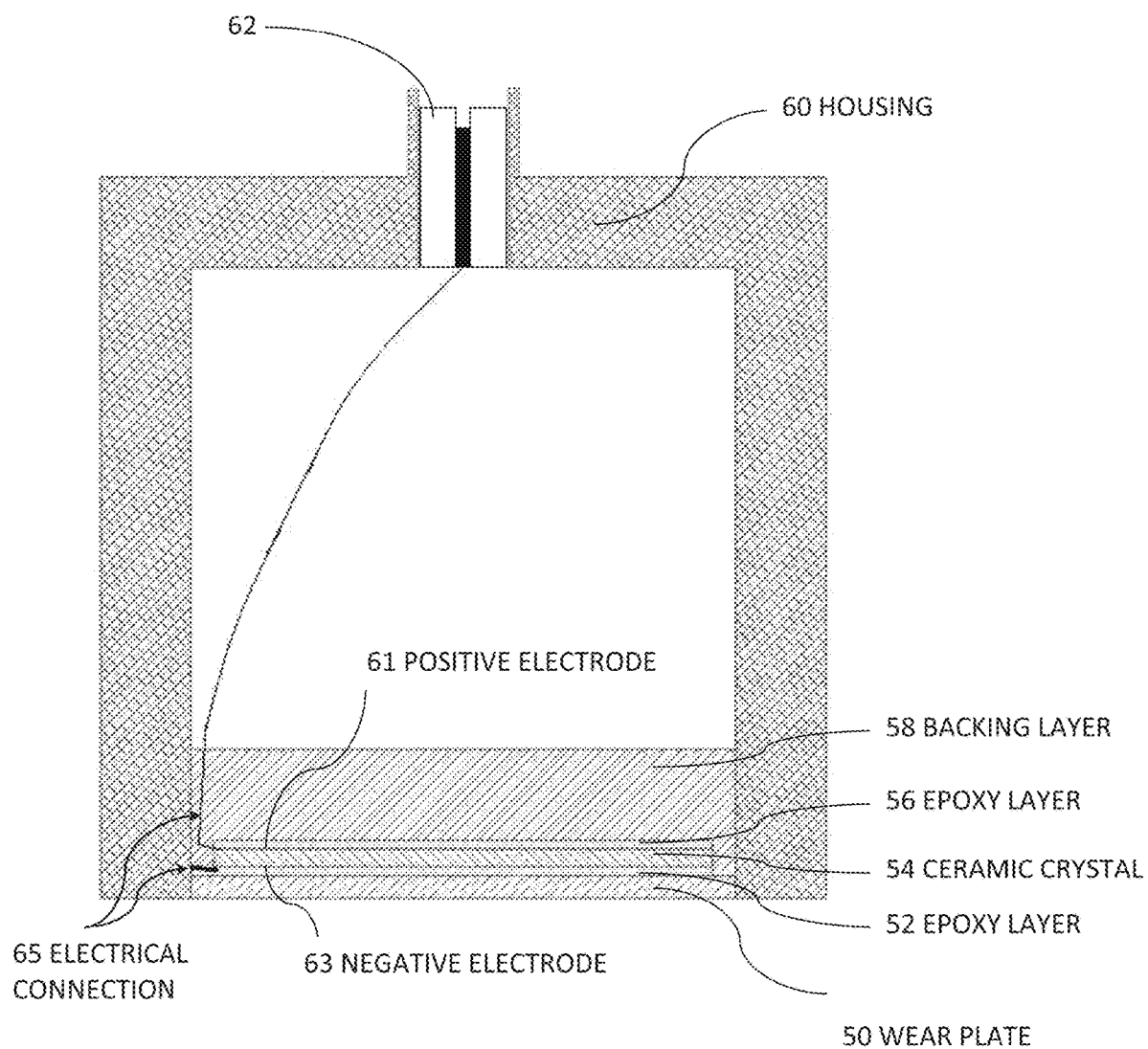
FIG. 2 is a cross-sectional diagram of a conventional ultrasonic transducer.

FIG. 2 is a cross-sectional diagram of a conventional ultrasonic transducer. This transducer has a wear plate 50 at a bottom end, epoxy layer 52, ceramic crystal 54 (made of, e.g. PZT), an epoxy layer 56, and a backing layer 58. On either side of the ceramic crystal, there is an electrode: a positive electrode 61 and a negative electrode 63. The epoxy layer 56 attaches backing layer 58 to the crystal 54. The entire assembly is contained in a housing 60 which may be made out of, for example, aluminum. An electrical adapter 62 provides connection for wires to pass through the housing and connect to leads (not shown) which attach to the crystal 54. Typically, backing layers are designed to add damping and to create a broadband transducer with uniform displacement across a wide range of frequency and are designed to suppress excitation at particular vibrational eigenmodes. Wear plates are usually designed as impedance transformers to better match the characteristic impedance of the medium into which the transducer radiates.

Figure 3B:
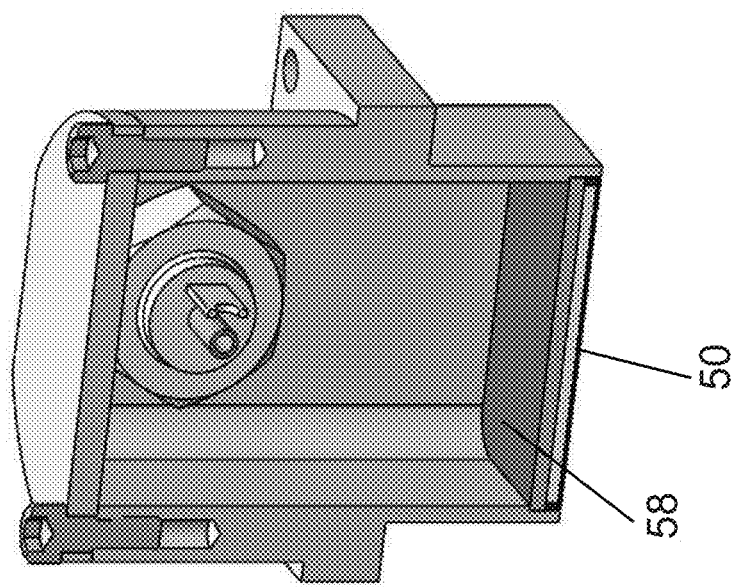
FIG. 3B is a cross-sectional diagram of an ultrasonic transducer structure that can be used in the present disclosure. An air gap is present within the transducer, and a backing layer and wear plate are present.
Figure 3A:
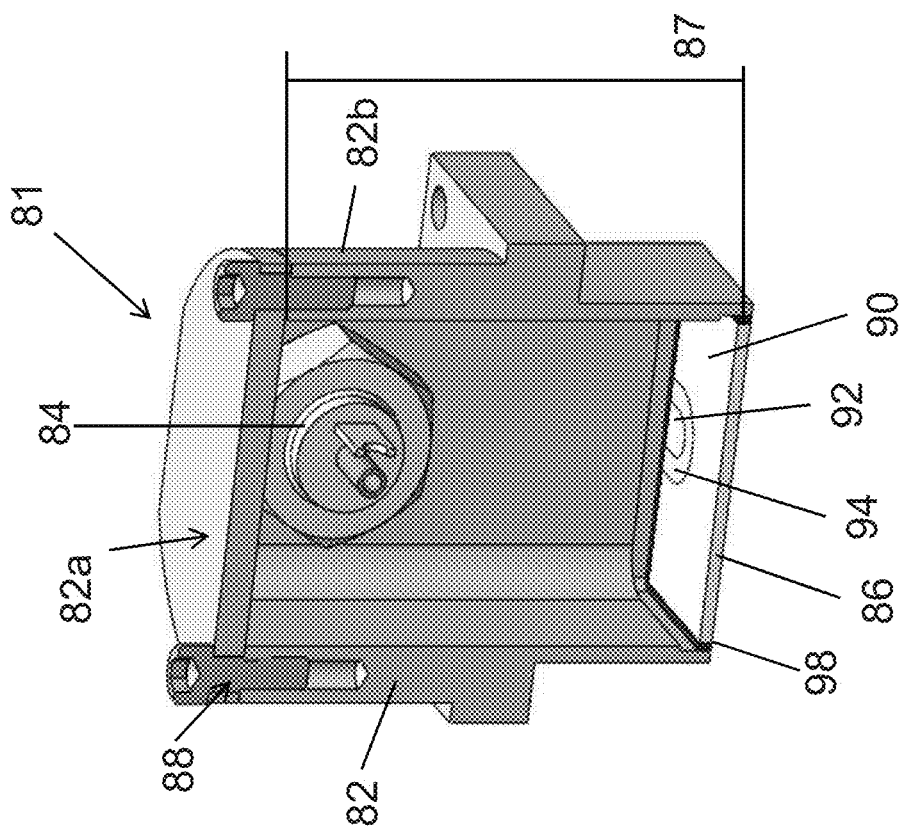
FIG. 3A is a cross-sectional diagram of an ultrasonic transducer structure that can be used in the present disclosure. An air gap is present within the transducer, and no backing layer or wear plate is present.

FIG. 3A is a cross-sectional view of an ultrasonic transducer 81 of the present disclosure, which can be used in acoustophoretic separator. Transducer 81 is shaped as a disc or a plate, and has an aluminum housing 82. The piezoelectric crystal is a mass of perovskite ceramic crystals, each consisting of a small, tetravalent metal ion, usually titanium or zirconium, in a lattice of larger, divalent metal ions, usually lead or barium, and $O^{2-}$ ions. As an example, a PZT (lead zirconate titanate) crystal 86 defines the bottom end of the transducer, and is exposed from the exterior of the housing. The crystal is supported on its perimeter by a small elastic layer 98, e.g. silicone or similar material, located between the crystal and the housing. Put another way, no wear layer is present.

Screws 88 attach an aluminum top plate 82a of the housing to the body 82b of the housing via threads. The top plate includes a connector 84 for powering the transducer. The top surface of the PZT crystal 86 is connected to a positive electrode 90 and a negative electrode 92, which are separated by an insulating material 94. The electrodes can be made from any conductive material, such as silver or nickel. Electrical power is provided to the PZT crystal 86 through the electrodes on the crystal. Note that the crystal 86 has no backing layer or epoxy layer as is present in FIG. 2. Put another way, there is an air gap 87 in the transducer between aluminum top plate 82a and the crystal 86 (i.e. the air gap is completely empty). A minimal backing 58 and/or wear plate 50 may be provided in some embodiments, as seen in FIG. 3B.

The transducer design can affect performance of the system. A typical transducer is a layered structure with the ceramic crystal bonded to a backing layer and a wear plate. Because the transducer is loaded with the high mechanical impedance presented by the fluid, the traditional design guidelines for wear plates, e.g., half wavelength thickness for standing wave applications or quarter wavelength thickness for radiation applications, and manufacturing methods may not be appropriate. Rather, in one embodiment of the present disclosure the transducers have no wear plate or backing, allowing the crystal to vibrate in one of its eigenmodes with a high Q-factor. The vibrating ceramic crystal/disk is directly exposed to the fluid flowing through the flow chamber.

Removing the backing (e.g. making the crystal air backed) also permits the ceramic crystal to vibrate at higher order modes of vibration with little damping (e.g. higher order modal displacement). In a transducer having a crystal with a backing, the crystal vibrates with a more uniform displacement, like a piston. Removing the backing allows the crystal to vibrate in a non-uniform displacement mode. The higher order the mode shape of the crystal, the more nodal lines the crystal has. The higher order modal displacement of the crystal creates more trapping lines, although the correlation of trapping line to node is not necessarily one to one, and driving the crystal at a higher frequency will not necessarily produce more trapping lines. See the discussion below with respect to FIGS. 8-9D.

In some embodiments, the crystal may have a backing that minimally affects the Q-factor of the crystal (e.g. less than 5%). The backing may be made of a substantially acoustically transparent material such as balsa wood, foam, or cork which allows the crystal to vibrate in a higher order mode shape and maintains a high Q-factor while still providing some mechanical support for the crystal. The backing layer may be a solid, or may be a lattice having holes through the layer, such that the lattice follows the nodes of the vibrating crystal in a particular higher order vibration mode, providing support at node locations while allowing the rest of the crystal to vibrate freely. The goal of the lattice work or acoustically transparent material is to provide support without lowering the Q-factor of the crystal or interfering with the excitation of a particular mode shape.

Placing the crystal in direct contact with the fluid also contributes to the high Q-factor by avoiding the dampening and energy absorption effects of the epoxy layer and the wear plate. Other embodiments may have wear plates or a wear surface to prevent the PZT, which contains lead, contacting the host fluid. This may be desirable in, for example, biological applications such as separating blood. Such applications might use a wear layer such as chrome, electrolytic nickel, or electroless nickel. Chemical vapor deposition could also be used to apply a layer of poly(p-xylylene) (e.g. Parylene) or other polymer. Organic and biocompatible coatings such as silicone or polyurethane are also usable as a wear surface. A glassy carbon wear layer may also be utilized. Glassy carbon, also known as vitreous carbon, is a non-graphitizing carbon which combines both glassy and ceramic properties with those of graphite. The most important properties are high temperature resistance, hardness (7 Mohs), low density, low electrical resistance, low friction and low thermal resistance. Glassy carbon also has extreme resistance to chemical attack and impermeability to gases and liquids.

In the present disclosure, the piezoelectric crystal used in each ultrasonic transducer is modified to be in the form of a segmented array of piezoelectric elements. This array is used to form a multidimensional acoustic standing wave or waves, which can be used for acoustophoresis. In particular, it is contemplated that each piezoelectric element can be used to generate a multi-dimensional acoustic standing wave.

FIG. 4 shows a monolithic, one-piece, single electrode piezoelectric crystal 200 that is used in ultrasonic transducers. The piezoelectric crystal has a substantially square shape, with a length 203 and a width 205 that are substantially equal to each other (e.g. about one inch). The crystal 200 has an inner surface 202, and the crystal also has an outer surface 204 on an opposite side of the crystal which is usually exposed to fluid flowing through the acoustophoretic device. The outer surface and the inner surface are relatively large in area, and the crystal is relatively thin (e.g. about 0.040 inches for a 2 MHz crystal).

FIG. 5 shows a piezoelectric crystal 200' of the present disclosure. The inner surface 202 of this piezoelectric crystal 200' is divided into a piezoelectric array 206 with a plurality of (i.e. at least two) piezoelectric elements 208. However, the array is still a single crystal. The piezoelectric elements 208 are separated from each other by one or more channels or kerfs 210 in the inner surface 202. The width of the channel (i.e. between piezoelectric elements) may be on the order of from about 0.001 inches to about 0.02 inches. The depth of the channel can be from about 0.001 inches to about 0.02 inches. In some instances, a potting material 212 (i.e., epoxy, Sil-Gel, and the like) can be inserted into the channels 210 between the piezoelectric elements. The potting material 212 is non-conducting, acts as an insulator between adjacent piezoelectric elements 208, and also acts to hold the separate piezoelectric elements 208 together. Here, the array 206 contains sixteen piezoelectric elements 208 (although any number of piezoelectric elements is possible), arranged in a rectangular 4×4 configuration (square is a subset of rectangular). Each of the piezoelectric elements 208 has substantially the same dimensions as each other. The overall array 200' has the same length 203 and width 205 as the single crystal illustrated in FIG. 4.

As described above, the transducer array is rectangular. However, this is not required. In other embodiments, the array can take other shapes/geometries. The piezoelectric elements can also be of other shapes/geometries, and does not need to be the same shape/geometry as the overall transducer array. It is also contemplated that the piezoelectric elements do not all need to have substantially the same dimensions. For example, the transducer array could be hexagonal, with equilateral triangular piezoelectric elements. The piezoelectrical elements that make up the array could be equilateral triangles, isosceles triangles, squares, rectangles, diamonds (four sides of equal length with two obtuse angles and two acute angles), hexagons, or trapezoids. The piezoelectric elements can be arranged in different geometries as well. For example, rectangular elements of one size could be arranged in a brick pattern (where the elements in one row are offset from the elements in an adjacent row), with rectangular elements of a second size being used to "fill in" gaps to form a rectangular transducer array. Hexagonal and equilateral triangular elements could be arranged to form a honeycomb pattern.

The pattern of the piezoelectric elements may be non-uniform as well. For example, a rectangular shape could be made from a row of trapezoids with a right trapezoid at each end. Similarly, a pattern could be formed by alternating the bases of isosceles triangles.

FIG. 6 shows another embodiment of a transducer 200". The transducer 200" is substantially similar to the transducer 200' of FIG. 5, except that the array 206 is formed from twenty-five piezoelectric elements 208 in a 5×5 configuration. Again, the overall array 200" has the same length 203 and width 205 as the single crystal illustrated in FIG. 4.

Each piezoelectric element in the piezoelectric array of the present disclosure may have individual electrical attachments (i.e. electrodes), so that each piezoelectric element can be individually controlled for phasing, frequency, and power. These elements can share a common ground electrode. This configuration allows for not only the generation of a multi-dimensional acoustic standing wave, but also improved control of the acoustic standing wave(s) generated by the array or by each piezoelectric element. In particular, it is contemplated that each piezoelectric element in the piezoelectric array can be operated at a frequency, with frequencies varying between some or all of the piezoelectric elements (i.e. same, equal, or different). In particular embodiments, the frequencies of all of the piezoelectric elements are within one order of magnitude of each other.

The control of phasing, power and frequency for each individual piezoelectric element in the transducer array would allow for manipulation of individual cells, such as T cells, NK cells, and other cell therapy therapeutic materials. This manipulation may also apply for microbeads. For instance, polystyrene microbeads typically have a density of 1.04 g/cc, while poly methyl methacrylate microbeads have a density of 1.18 g/cc. This small difference in density greatly changes the contrast factor of these two types of microbeads. Sorting these microbeads using the phasing, power, and frequency control of a piezoelectric transducer array would allow for individual separation of these beads and perhaps the cells that are attached to them as well. This type of phased array would also allow for cytometry, where cells with different contrast factors (e.g. white blood cells, red blood cells, and platelets) are separated individually by the array of piezoelectric elements.

The piezoelectric array can be formed from a monolithic piezoelectric crystal by making cuts across one surface so as to divide the surface of the piezoelectric crystal into separate elements. The cutting of the surface may be performed through the use of a saw, an end mill, or other means to remove material from the surface and leave discrete elements of the piezoelectric crystal between the channels/grooves that are thus formed.

Figure 21:
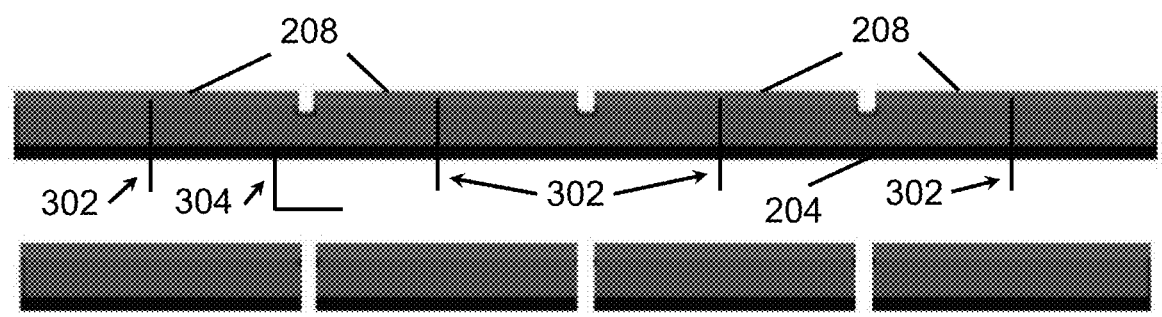
FIG. 21 is a picture illustrating a kerfed crystal (top) versus a transducer array that has piezoelectric elements joined together by a potting material (bottom).

As explained above, a potting material may be incorporated into the channels/grooves between the elements to form a composite material. For example, the potting material can be a polymer, such as epoxy. In particular embodiments, the piezoelectric elements 208 are individually physically isolated from each other. This structure can be obtained by filling the channels 210 with the potting material, then cutting, sanding or grinding the outer surface 204 down to the channels. As a result, the piezoelectric elements are joined to each other through the potting material, and each element is an individual component of the array. Put another way, each piezoelectric element is physically separated from surrounding piezoelectric elements by the potting material. FIG. 21 is a cross-sectional view comparing these two embodiments. On top, a crystal as illustrated in FIG. 5 is shown. The crystal is kerfed into four separate piezoelectric elements 208 on the inner surface 202, each being connected to an individual electrode 302. The four elements 208 share a common outer surface 204, which share a common ground electrode 304. On the bottom, the four piezoelectric elements 208 are physically isolated from each other by potting material 212. No common surface is shared between the four elements.

In the present systems, the system is operated at a voltage such that the particles are trapped in the ultrasonic standing wave, i.e., remain in a stationary position. The particles are collected in along well defined trapping lines, separated by half a wavelength. Within each nodal plane, the particles are trapped in the minima of the acoustic radiation potential. The axial component of the acoustic radiation force drives the particles, with a positive contrast factor, to the pressure nodal planes, whereas particles with a negative contrast factor are driven to the pressure anti-nodal planes. The radial or lateral component of the acoustic radiation force is the force that traps the particle. In systems using typical transducers, the radial or lateral component of the acoustic radiation force is typically several orders of magnitude smaller than the axial component of the acoustic radiation force. However, the lateral force in the devices of the present disclosure can be significant, on the same order of magnitude as the axial force component, and is sufficient to overcome the fluid drag force at linear velocities of up to 1 cm/s. As discussed above, the lateral force can be increased by driving the transducer in higher order mode shapes, as opposed to a form of vibration where the crystal effectively moves as a piston having a uniform displacement. The acoustic pressure is proportional to the driving voltage of the transducer. The electrical power is proportional to the square of the voltage.

During operation, the piezoelectric arrays of the present disclosure can be driven so that the piezoelectric elements are in phase with each other. In other words, each piezoelectric element creates a multi-dimensional acoustic standing wave that has the same frequency and no time shift. In other embodiments, the piezoelectric elements can be out of phase with each other, i.e. there is a different frequency or time shift, or they have a different phase angle. As described further below, in more specific embodiments the elements in the array are arranged in groups or sets that are out of phase by multiples of 90° (i.e. 90° and/or 180°). It is also contemplated that the piezoelectric array can be rotated. In this regard, there can be some spacing between adjacent multi-dimensional acoustic standing waves generated by adjacent piezoelectric elements. Rotation of the array permits the acoustic standing waves to "travel" through and treat the fluid in these spaces between waves, so that the entire flow path past the transducer array can be acoustically treated.

In embodiments, the pulsed voltage signal driving the transducer can have a sinusoidal, square, sawtooth, or triangle waveform; and have a frequency of 500 kHz to 10 MHz. The pulsed voltage signal can be driven with pulse width modulation, which produces any desired waveform. The pulsed voltage signal can also have amplitude or frequency modulation start/stop capability to eliminate streaming.

Figure 7:
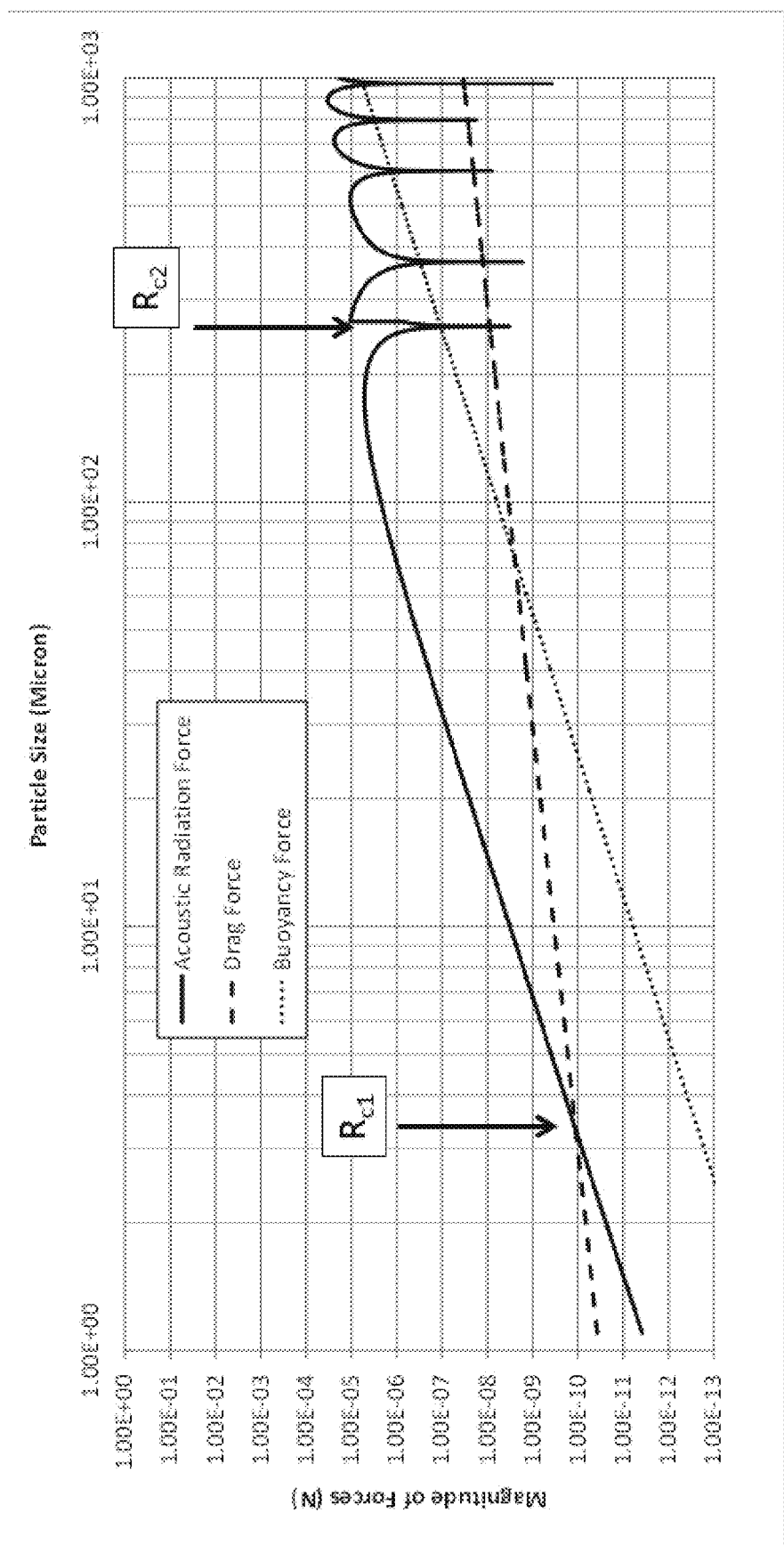
FIG. 7 is a graph showing the relationship of the acoustic radiation force, gravity/buoyancy force, and Stokes' drag force to particle size. The horizontal axis is in microns (µm) and the vertical axis is in Newtons (N).

FIG. 7 is a log-log graph (logarithmic y-axis, logarithmic x-axis) that shows the scaling of the acoustic radiation force, fluid drag force, and buoyancy force with particle radius. Calculations are done for a typical SAE-30 oil droplet used in experiments. The buoyancy force is a particle volume dependent force, and is therefore negligible for particle sizes on the order of micron, but grows, and becomes significant for particle sizes on the order of hundreds of microns. The fluid drag force scales linearly with fluid velocity, and therefore typically exceeds the buoyancy force for micron sized particles, but is negligible for larger sized particles on the order of hundreds of microns. The acoustic radiation force scaling is different. When the particle size is small, Gor'kov's equation is accurate and the acoustic trapping force scales with the volume of the particle. Eventually, when the particle size grows, the acoustic radiation force no longer increases with the cube of the particle radius, and will rapidly vanish at a certain critical particle size. For further increases of particle size, the radiation force increases again in magnitude but with opposite phase (not shown in the graph). This pattern repeats for increasing particle sizes.

Initially, when a suspension is flowing through the system with primarily small micron sized particles, it is necessary for the acoustic radiation force to balance the combined effect of fluid drag force and buoyancy force for a particle to be trapped in the standing wave. In FIG. 7 this happens for a particle size of about 3.5 micron, labeled as $R_{c1}$. The graph then indicates that all larger particles will be trapped as well. Therefore, when small particles are trapped in the standing wave, particles coalescence/clumping/aggregation/agglomeration takes place, resulting in continuous growth of effective particle size. As the particle size grows, the acoustic radiation force reflects off the particle, such that large particles will cause the acoustic radiation force to decrease. Particle size growth continues until the buoyancy force becomes dominant, which is indicated by a second critical particle size, $R_{c2}$, at which size the particles will rise or sink, depending on their relative density with respect to the host fluid. As the particles rise or sink, they no longer reflect the acoustic radiation force, so that the acoustic radiation force then increases. Not all particles will drop out, and those remaining particles will continue to grow in size as well. This phenomenon explains the quick drops and rises in the acoustic radiation force beyond size $R_{c2}$. Thus, FIG. 7 explains how small particles can be trapped continuously in a standing wave, aggregate into larger particles or clumps, and continuously fall out of the multi-dimensional acoustic standing wave due to gravitational separation.

The size, shape, and thickness of the transducer determine the transducer displacement at different frequencies of excitation, which in turn affects oil separation efficiency. Typically, the transducer is operated at frequencies near the thickness resonance frequency (half wavelength). Gradients in transducer displacement typically result in more places for oil to be trapped. Higher order modal displacements generate three-dimensional acoustic standing waves with strong gradients in the acoustic field in all directions, thereby creating equally strong acoustic radiation forces in all directions, leading to multiple trapping lines, where the number of trapping lines correlate with the particular mode shape of the transducer.

Figure 8:
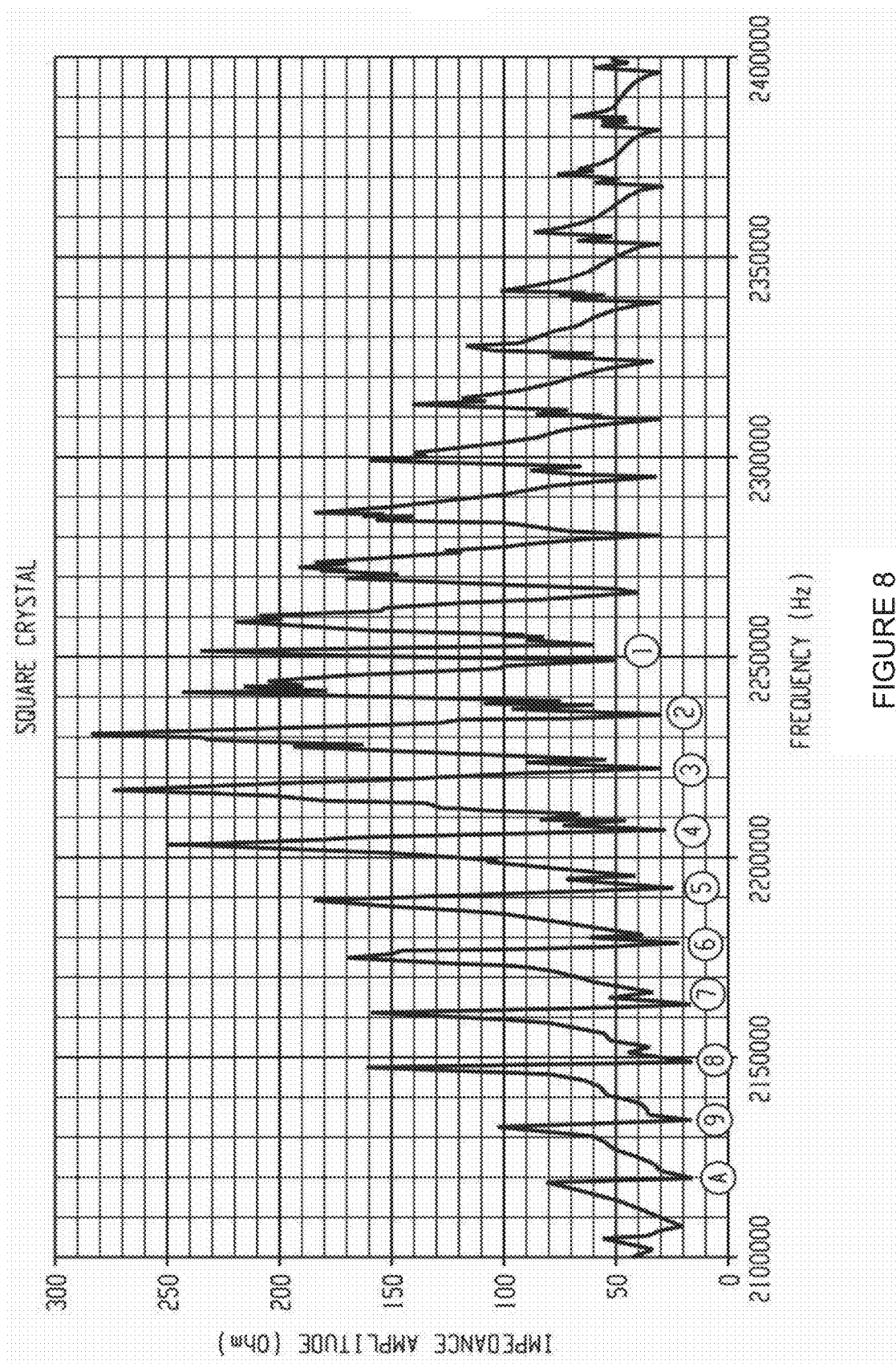
FIG. 8 is a graph of electrical impedance amplitude versus frequency for a square transducer driven at different frequencies.

FIG. 8 shows the measured electrical impedance amplitude of a 1" square PZT-8 2-MHz transducer as a function of frequency in the vicinity of the 2.2 MHz transducer resonance. The minima in the transducer electrical impedance correspond to acoustic resonances of the water column and represent potential frequencies for operation. Numerical modeling has indicated that the transducer displacement profile varies significantly at these acoustic resonance frequencies, and thereby directly affects the acoustic standing wave and resulting trapping force. Since the transducer operates near its thickness resonance, the displacements of the electrode surfaces are essentially out of phase. The typical displacement of the transducer electrodes is not uniform and varies depending on frequency of excitation. As an example, at one frequency of excitation with a single line of trapped oil droplets, the displacement has a single maximum in the middle of the electrode and minima near the transducer edges. At another excitation frequency, the transducer profile has multiple maxima leading to multiple trapped lines of oil droplets. Higher order transducer displacement patterns result in higher trapping forces and multiple stable trapping lines for the captured oil droplets.

To investigate the effect of the transducer displacement profile on acoustic trapping force and oil separation efficiencies, an experiment was repeated ten times, with all conditions identical except for the excitation frequency. Ten consecutive acoustic resonance frequencies, indicated by circled numbers 1-9 and letter A on FIG. 8, were used as excitation frequencies. These oscillations in the impedance correspond to the resonance of the acoustophoretic system. With the length of the acoustophoretic system being 2", the oscillations are spaced about 15 kHz apart. The conditions were experiment duration of 30 min, a 1000 ppm oil concentration of approximately 5-micron SAE-30 oil droplets, a flow rate of 500 ml/min, and an applied power of 20 W in a 1-inch wide×2-inch long cross-section.

Figure 9A:
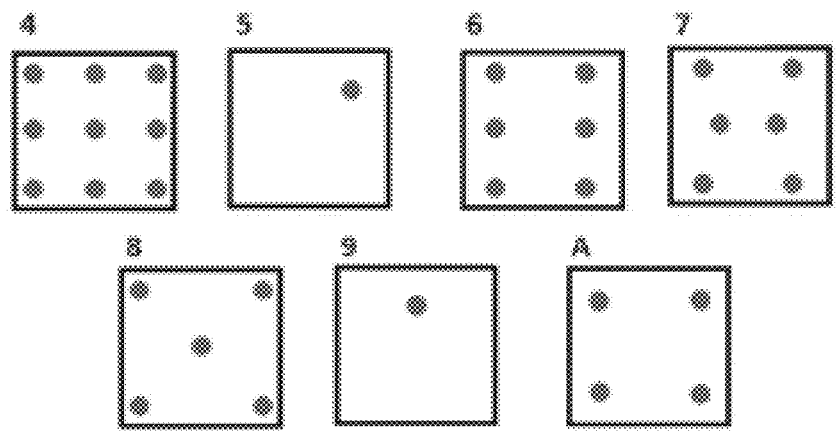
FIG. 9A illustrates the trapping line configurations for seven of the minima amplitudes of FIG. 8 from the direction orthogonal to fluid flow.

As the emulsion passed by the transducer, the trapping lines of oil droplets were observed and characterized. The characterization involved the observation and pattern of the number of trapping lines across the fluid channel, as shown in FIG. 9A, for seven of the ten resonance frequencies identified in FIG. 8.

Figure 9B:
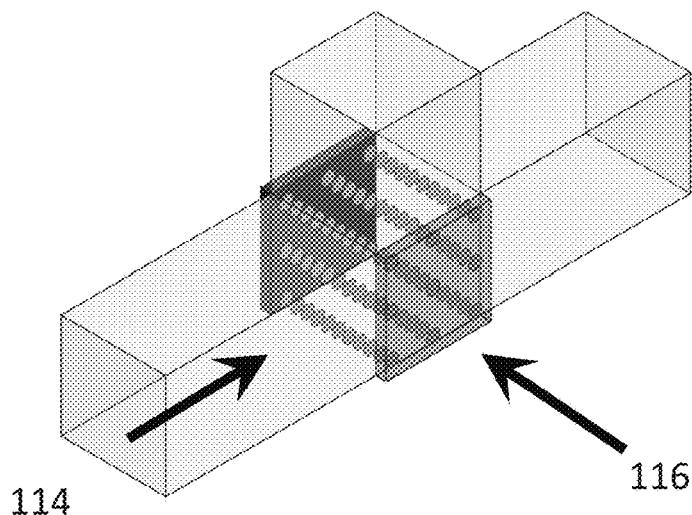
FIG. 9B is a perspective view illustrating the separator. The fluid flow direction and the trapping lines are shown.
Figure 9C:
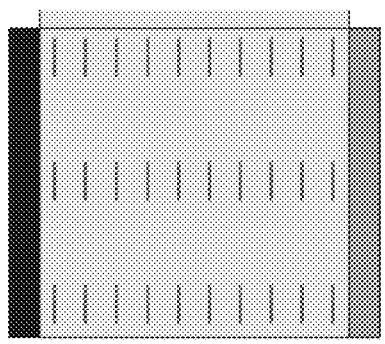
FIG. 9C is a view from the fluid inlet along the fluid flow direction (arrow 114) of FIG. 9B, showing the trapping nodes of the standing wave where particles would be captured.
Figure 9D:
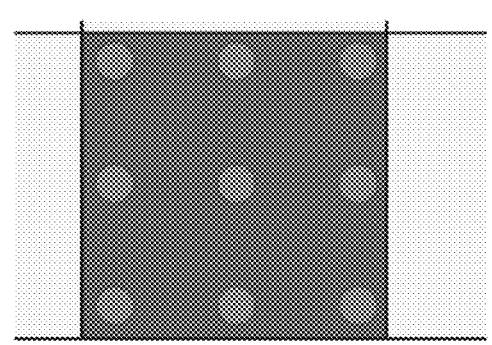
FIG. 9D is a view taken through the transducers face at the trapping line configurations, along arrow 116 as shown in FIG. 9B.

FIG. 9B shows an isometric view of the system in which the trapping line locations are being determined. FIG. 9C is a view of the system as it appears when looking down the inlet, along arrow 114. FIG. 9D is a view of the system as it appears when looking directly at the transducer face, along arrow 116. The trapping lines shown in FIGS. 9B-9D are those produced at frequency 4 in FIG. 8 and FIG. 9A.

The effect of excitation frequency clearly determines the number of trapping lines, which vary from a single trapping line at the excitation frequency of acoustic resonance 5 and 9, to nine trapping lines for acoustic resonance frequency 4. At other excitation frequencies four or five trapping lines are observed. Different displacement profiles of the transducer can produce different (more) trapping lines in the standing waves, with more gradients in displacement profile generally creating higher trapping forces and more trapping lines.

Figure 10A:
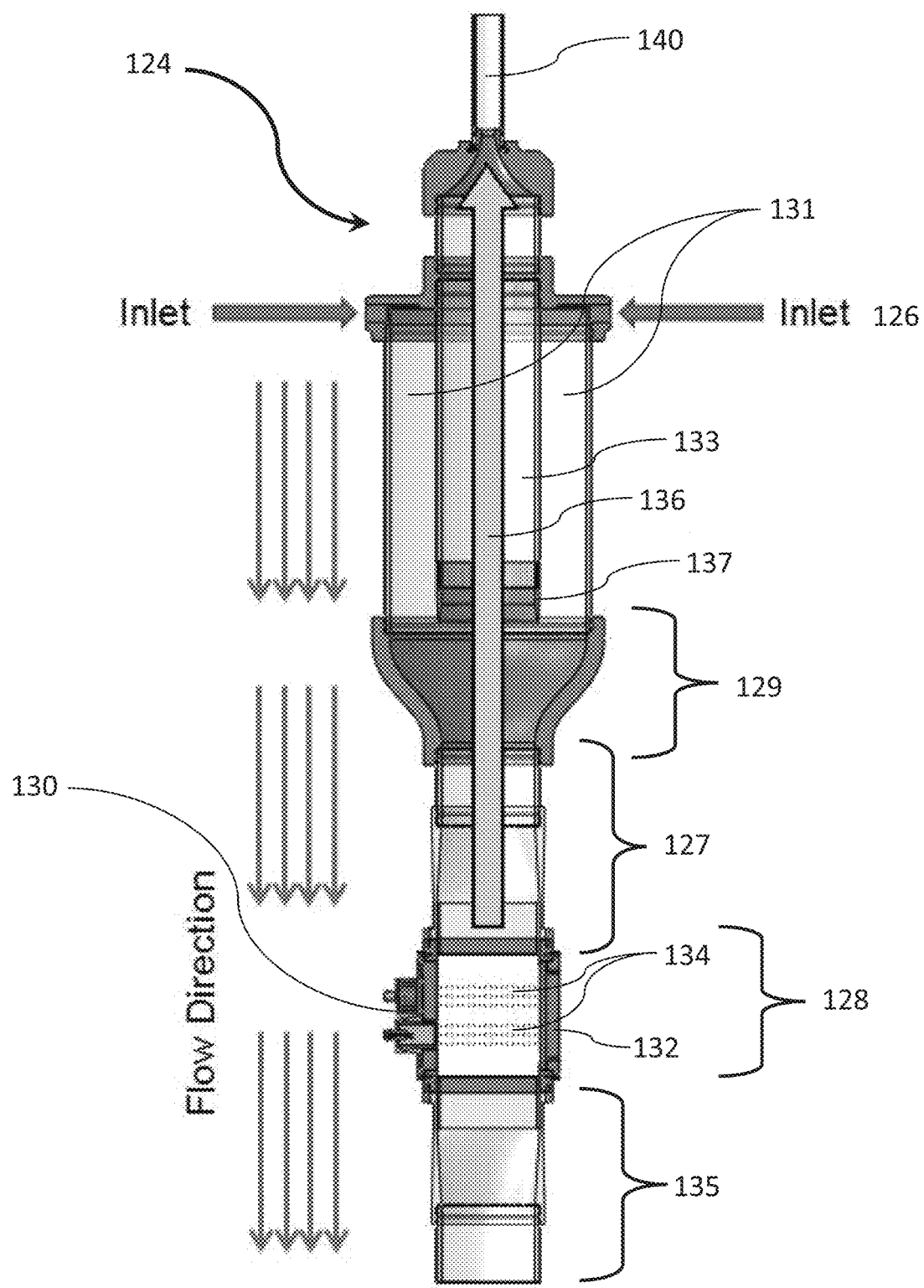
FIG. 10A shows an acoustophoretic separator for separating buoyant materials.

Table 1 summarizes the findings from an oil trapping experiment using a system similar to FIG. 10A. An important conclusion is that the oil separation efficiency of the acoustic separator is directly related to the mode shape of the transducer. Higher order displacement profiles generate larger acoustic trapping forces and more trapping lines resulting in better efficiencies. A second conclusion, useful for scaling studies, is that the tests indicate that capturing 5 micron oil droplets at 500 ml/min requires 10 Watts of power per square-inch of transducer area per 1" of acoustic beam span. The main dissipation is that of thermo-viscous absorption in the bulk volume of the acoustic standing wave. The cost of energy associated with this flow rate is 0.500 kWh per cubic meter.

TABLE 1

Trapping Pattern Capture Efficiency Study

| Resonance Peak Location | Total Power Input (Watts) | # of Trapping Lines | Flow rate (ml/min) | Duration (min) | Capture Efficiency (%) |
|---|---|---|---|---|---|
| 4 | 20 | 9 | 500 | 30 | 91% |
| 8 | 20 | 5 | 500 | 30 | 58% |
| A | 20 | 4 | 500 | 30 | 58% |
| 9 | 20 | 2 | 500 | 30 | 37% |

A 4" by 2.5" flow cross sectional area intermediate scale apparatus 124 for separating a host fluid from a buoyant fluid or particulate is shown in FIG. 10A. The acoustic path length is 4". The apparatus is shown here in an orientation where the flow direction is downwards, which is used for separating less-dense particles from the host fluid. However, the apparatus may be essentially turned upside down to allow separation of particles which are heavier than the host fluid. Instead of a buoyant force in an upward direction, the weight of the agglomerated particles due to gravity pulls them downward. It should be noted that this embodiment is depicted as having an orientation in which fluid flows vertically. However, it is also contemplated that fluid flow may be in a horizontal direction, or at an angle.

A particle-containing fluid enters the apparatus through inlets 126 into an annular plenum 131. The annular plenum has an annular inner diameter and an annular outer diameter. It is noted that the term "annular" is used here to refer to the area between two shapes, and the plenum does not need to be circular. Two inlets are visible in this illustration, though it is contemplated that any number of inlets may be provided as desired. In particular embodiments, four inlets are used. The inlets are radially opposed and oriented.

A contoured nozzle wall 129 reduces the outer diameter of the flow path in a manner that generates higher velocities near the wall region and reduces turbulence, producing near plug flow as the fluid velocity profile develops, i.e. the fluid is accelerated downward in the direction of the centerline with little to no circumferential motion component and low flow turbulence. This generates a chamber flow profile that is optimum for acoustic separation and particle collection. The fluid passes through connecting duct 127 and into a flow/separation chamber 128. As seen in the zoomed-in contoured nozzle 129 in FIG. 10B, the nozzle wall also adds a radial motion component to the suspended particles, moving the particles closer to the centerline of the apparatus and generating more collisions with rising, buoyant agglomerated particles. This radial motion will allow for optimum scrubbing of the particles from the fluid in the connecting duct 127 prior to reaching the separation chamber. The contoured nozzle wall 129 directs the fluid in a manner that generates large scale vortices at the entrance of the collection duct 133 to also enhance particle collection. Generally, the flow area of the device 124 is designed to be continually decreasing from the annular plenum 131 to the separation chamber 128 to assure low turbulence and eddy formation for better particle separation, agglomeration, and collection. The nozzle wall has a wide end and a narrow end. The term scrubbing is used to describe the process of particle/droplet agglomeration, aggregation, clumping or coalescing, that occurs when a larger particle/droplet travels in a direction opposite to the fluid flow and collides with smaller particles, in effect scrubbing the smaller particles out of the suspension.

Returning to FIG. 10A, the flow/separation chamber 128 includes a transducer array 130 and reflector 132 on opposite sides of the chamber. In use, multi-dimensional standing waves 134 are created between the transducer array 130 and reflector 132. These standing waves can be used to agglomerate particles, and this orientation is used to agglomerate particles that are buoyant (e.g. oil). Fluid, containing residual particles, then exits through flow outlet 135.

As the buoyant particles agglomerate, they eventually overcome the combined effect of the fluid flow drag forces and acoustic radiation force, and their buoyant force 136 is sufficient to cause the buoyant particles to rise upwards. In this regard, a collection duct 133 is surrounded by the annular plenum 131. The larger particles will pass through this duct and into a collection chamber 140. This collection chamber can also be part of an outlet duct. The collection duct and the flow outlet are on opposite ends of the apparatus.

It should be noted that the buoyant particles formed in the separation chamber 128 subsequently pass through the connecting duct 127 and the nozzle wall 129. This causes the incoming flow from the annular plenum to flow over the rising agglomerated particles due to the inward radial motion imparted by the nozzle wall.

The transducer setup of the present disclosure creates a three dimensional pressure field which includes standing waves perpendicular to the fluid flow. The pressure gradients are large enough to generate acoustophoretic forces orthogonal to the standing wave direction (i.e., the acoustophoretic forces are parallel to the fluid flow direction) which are of the same order of magnitude as the acoustophoretic forces in the wave direction. This permits enhanced particle trapping, clumping and collection in the flow chamber and along well-defined trapping lines, as opposed to merely trapping particles in collection planes as in conventional devices. The particles have significant time to move to nodes or antinodes of the standing waves, generating regions where the particles can concentrate, agglomerate, and/or coalesce, and then buoyancy/gravity separate.

In some embodiments, the fluid flow has a Reynolds number of up to 1500, i.e. laminar flow is occurring. For practical application in industry, the Reynolds number is usually from 10 to 1500 for the flow through the system. The particle movement relative to the fluid motion generates a Reynolds number much less than 1.0. The Reynolds number represents the ratio of inertial flow effects to viscous effects in a given flow field. For Reynolds numbers below 1.0, viscous forces are dominant in the flow field. This results in significant damping where shear forces are predominant throughout the flow. This flow where viscous forces are dominant is called Stokes flow. The flow of molasses is an example. Wall contouring and streamlining have very little importance under such conditions. This is associated with the flow of very viscous fluids or the flow in very tiny passages, like MEMS devices. Inlet contouring has little importance. The flow of the particles relative to the fluid in an acoustophoretic particle separator will be Stokes flow because both the particle diameters and the relative velocities between the particles and fluid are very small. On the other hand, the Reynolds number for the flow through the system will be much greater than 1.0 because the fluid velocity and inlet diameter are much larger.

For Reynolds numbers much greater than 1.0, viscous forces are dominant only where the flow is in contact with the surface. This viscous region near the surface is called a boundary layer and was first recognized by Ludwig Prandtl. In duct flow, the flow will be laminar if the Reynolds number is significantly above 1.0 and below 2300 for fully developed flow in the duct. The wall shear stress at the wall will diffuse into the stream with distance. At the inlet of the duct, flow velocity starts off uniform. As the flow moves down the duct, the effect of wall viscous forces will diffuse inward towards the centerline to generate a parabolic velocity profile. This parabolic profile will have a peak value that is twice the average velocity. The length required for the parabolic profile to develop is a function of the Reynolds number. For a Reynolds number of 20, which is typical for CHO operation, the development length will be 1.2 duct diameters. Thus, fully developed flow happens very quickly. This peak velocity in the center can be detrimental to acoustic particle separation. Also, at laminar flow Reynolds numbers turbulence, can occur and flow surface contouring is very important in controlling the flow. For these reasons, the separator was designed with an annular inlet plenum and collector tube.

Figure 10B:
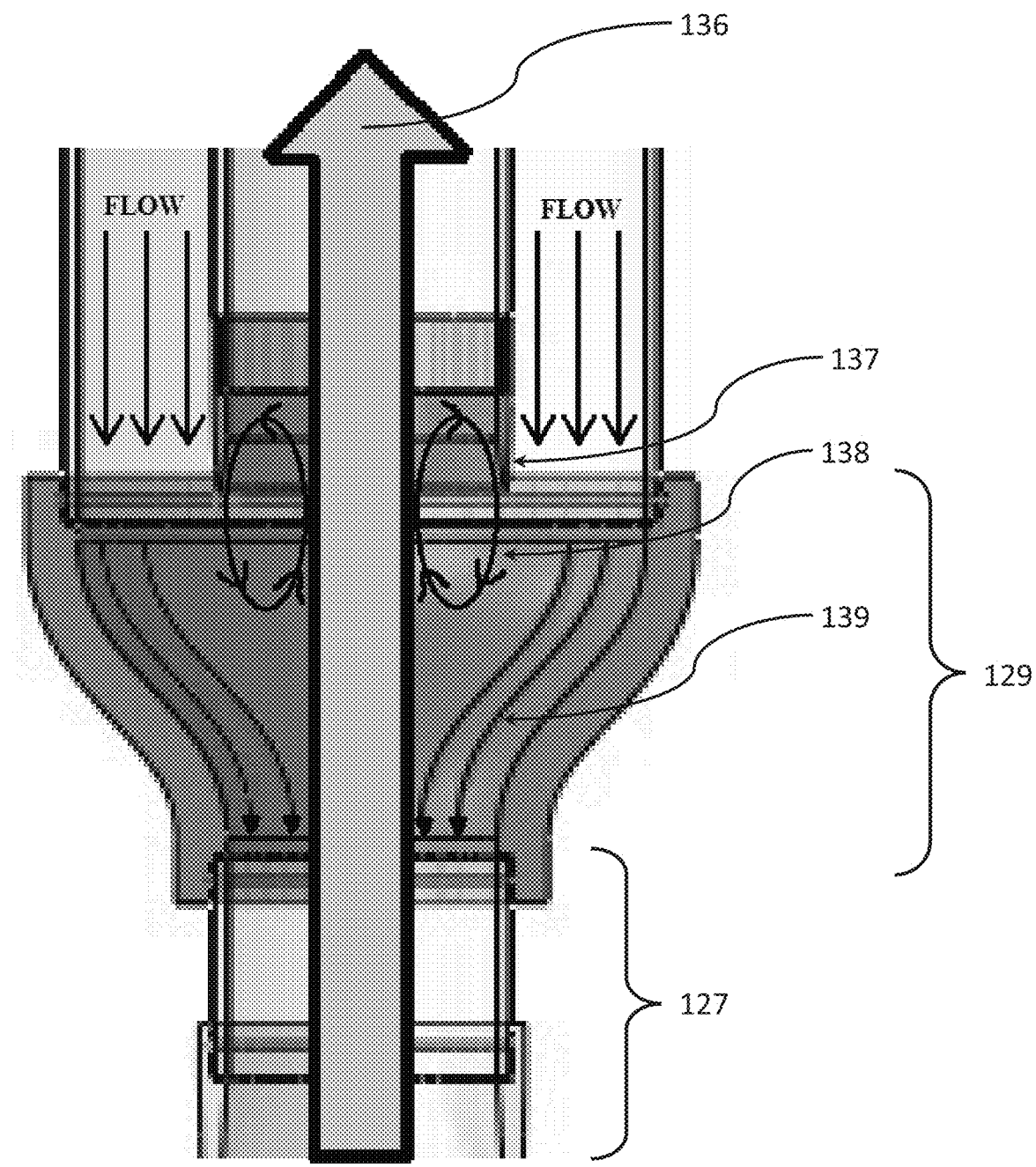
FIG. 10B is a magnified view of fluid flow near the intersection of the contoured nozzle wall 129 and the collection duct 137.

The large annular plenum is followed by an inlet wall nozzle that accelerates and directs the fluid inward toward the centerline as shown in FIG. 10B. The wall contour will have a large effect on the profile. The area convergence increases the flow average velocity, but it is the wall contour that determines the velocity profile. The nozzle wall contour will be a flow streamline, and is designed with a small radius of curvature in the separator.

The transducer(s) is/are used to create a pressure field that generates forces of the same order of magnitude both orthogonal to the standing wave direction and in the standing wave direction. When the forces are roughly the same order of magnitude, particles of size 0.1 microns to 300 microns will be moved more effectively towards regions of agglomeration ("trapping lines"). Because of the equally large gradients in the orthogonal acoustophoretic force component, there are "hot spots" or particle collection regions that are not located in the regular locations in the standing wave direction between the transducer 130 and the reflector 132. Hot spots are located at the minima of acoustic radiation potential. Such hot spots represent particle collection locations.

One application of the acoustophoretic device is the separation of a biological therapeutic protein from the biologic cells that produce the protein. In this regard, current methods of separation require filtration or centrifugation, either of which can damage cells, releasing protein debris and enzymes into the purification process and increasing the load on downstream portions of the purification system. It is desirable to be able to process volumes having higher cell densities, because this permits collection of larger amounts of the therapeutic protein and better cost efficiencies.

Figure 11A:
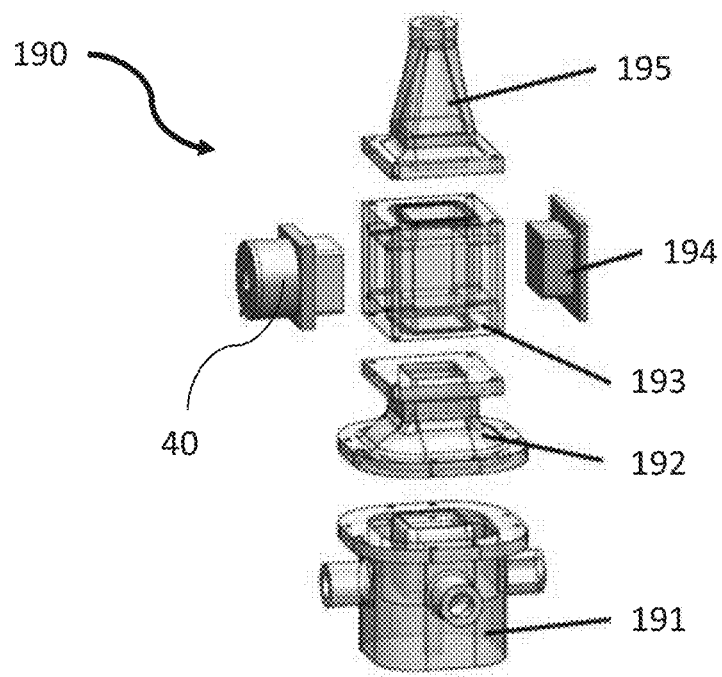
FIG. 11A shows an exploded view of an acoustophoretic separator used in Bio-Pharma applications.
Figure 11B:
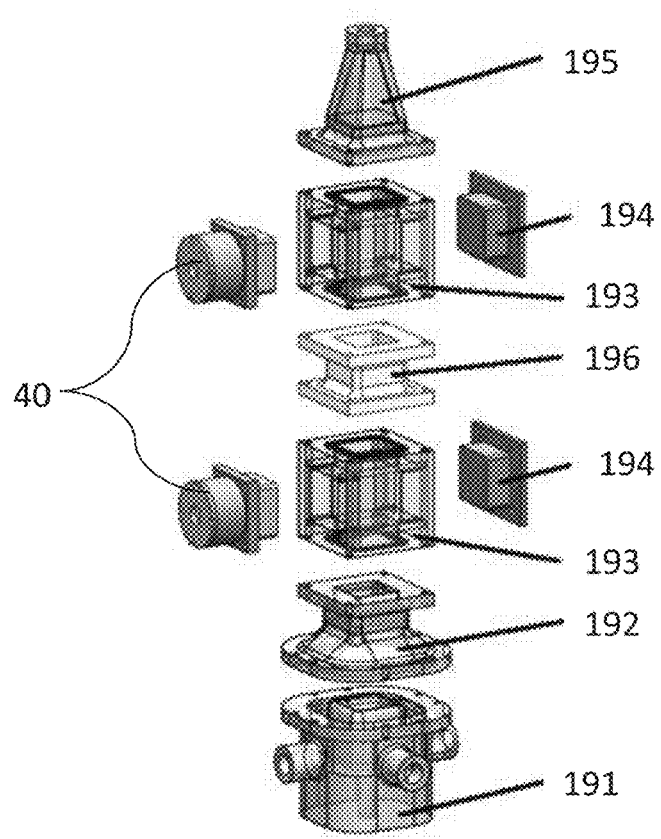
FIG. 11B shows an exploded view of a stacked acoustophoretic separator with two acoustic chambers.

FIG. 11A and FIG. 11B are exploded views showing the various parts of acoustophoretic separators. FIG. 11A has only one separation chamber, while FIG. 11B has two separation chambers.

Referring to FIG. 11A, fluid enters the separator 190 through a four-port inlet 191. An annular plenum is also visible here. A transition piece 192 is provided to create plug flow through the separation chamber 193. This transition piece includes a contoured nozzle wall, like that described above in FIG. 10A, which has a curved shape. A transducer 40 and a reflector 194 are located on opposite walls of the separation chamber. Fluid then exits the separation chamber 193 and the separator through outlet 195. The separation chamber has a rectangular-shaped flow path geometry.

FIG. 11B has two separation chambers 193. A system coupler 196 is placed between the two chambers 193 to join them together.

Acoustophoretic separation has been tested on different lines of Chinese hamster ovary (CHO) cells. In one experiment, a solution with a starting cell density of $8.09 \times 10^6$ cells/mL, a turbidity of 1,232 NTU, and cell viability of roughly 75% was separated using a system as depicted in FIG. 11A. The transducers were 2 MHz crystals, run at approximately 2.23 MHz, drawing 24-28 Watts. A flow rate of 25 mL/min was used. The result of this experiment is shown in FIG. 12A.

In another experiment, a solution with a starting cell density of $8.09 \times 10^6$ cells/mL, a turbidity of 1,232 NTU, and cell viability of roughly 75% was separated. This CHO cell line had a bi-modal particle size distribution (at size 12 μm and 20 μm). The result is shown in FIG. 12B.

Figure 12A:
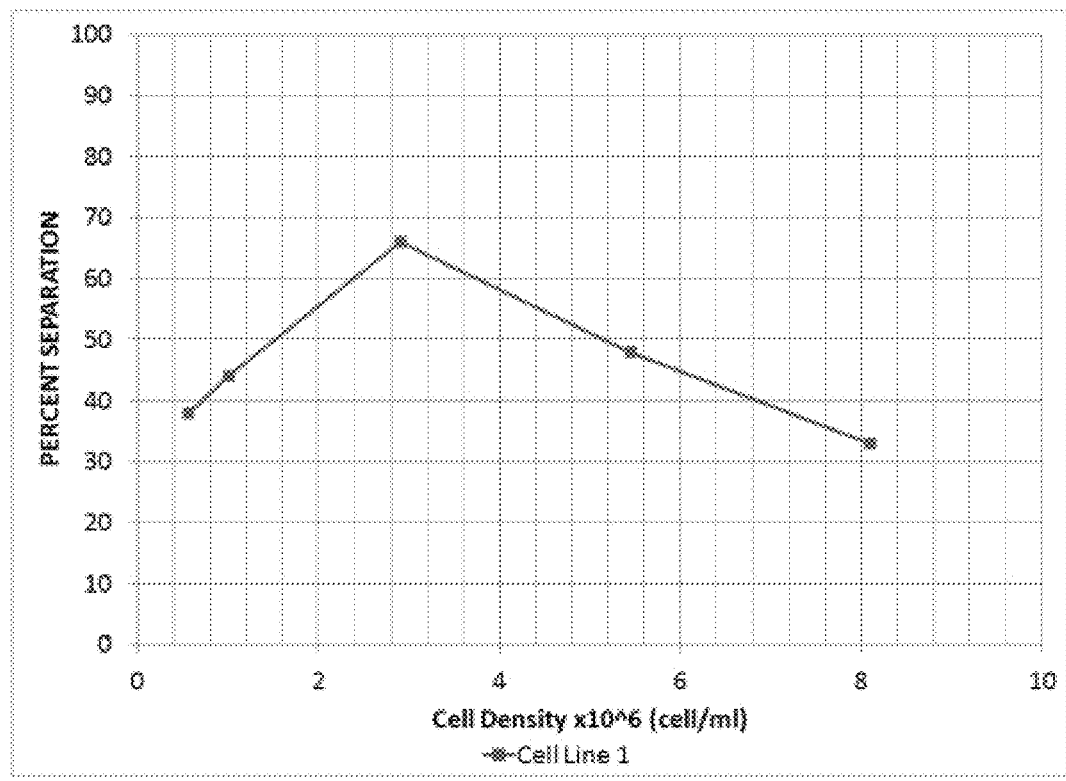
FIG. 12A is a graph showing the efficiency of removing cells from a medium using a Beckman Coulter Cell Viability Analyzer for one experiment.
Figure 12B:
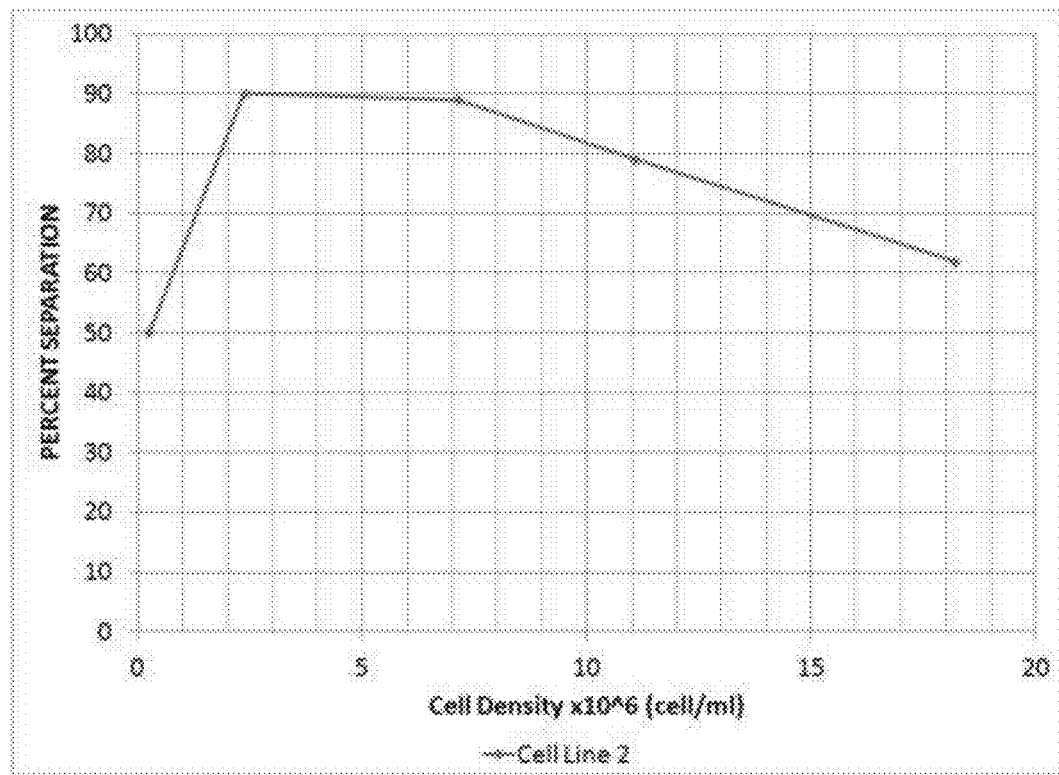
FIG. 12B is a graph showing the efficiency of removing cells from a medium using a Beckman Coulter Cell Viability Analyzer for another experiment.

FIG. 12A and FIG. 12B were produced by a Beckman Coulter Cell Viability Analyzer. Other tests revealed that frequencies of 1 MHz and 3 MHz were not as efficient as 2 MHz at separating the cells from the fluid.

In other tests at a flow rate of 10 L/hr, 99% of cells were captured with a confirmed cell viability of more than 99%. Other tests at a flow rate of 50 mL/min (i.e. 3 L/hr) obtained a final cell density of $3 \times 10^6$ cells/mL with a viability of nearly 100% and little to no temperature rise. In yet other tests, a 95% reduction in turbidity was obtained at a flow rate of 6 L/hr.

Testing on the scaled unit shown in FIG. 10A-10B was performed using yeast as a simulant for CHO for the biological applications. For these tests, at a flow rate of 15 L/hr, various frequencies were tested as well as power levels. Table 2 shows the results of the testing.

TABLE 2

| 2.5" × 4" System results at 15 L/hr Flow rate | | | |
|---|---|---|---|
| Frequency (MHz) | 30 Watts | 37 Watts | 45 Watts |
| 2.2211 | 93.9 | 81.4 | 84.0 |
| 2.2283 | 85.5 | 78.7 | 85.4 |
| 2.2356 | 89.1 | 85.8 | 81.0 |
| 2.243 | 86.7 | — | 79.6 |

In biological applications, many parts, e.g. the tubing leading to and from the housing, inlets, exit plenum, and entrance plenum, may all be disposable, with only the transducer and reflector to be cleaned for reuse. Avoiding centrifuges and filters allows better separation of the CHO cells without lowering the viability of the cells. The form factor of the acoustophoretic separator is also smaller than a filtering system, allowing the CHO separation to be miniaturized. The transducers may also be driven to create rapid pressure changes to prevent or clear blockages due to agglomeration of CHO cells. The frequency of the transducers may also be varied to obtain optimal effectiveness for a given power.

The following examples are provided to illustrate the apparatuses, components, and methods of the present disclosure. The examples are merely illustrative and are not intended to limit the disclosure to the materials, conditions, or process parameters set forth therein.

EXAMPLES

A two-dimensional numerical model was developed for the acoustophoretic device using COMSOL simulation software. The model is illustrated in FIG. 13. The device included an aluminum wall 222, and a stainless steel reflector 224 opposite the wall. Embedded in the wall was a piezoelectric transducer 230. As illustrated here, the transducer is in the form of a 4-element piezoelectric array. The wall 222 and the reflector 224 define a flow chamber, with arrow 225 indicating the flow direction of fluid through the chamber. The piezoelectric transducer was in direct contact with the fluid. Channels/kerfs 210 and potting material 212 are also illustrated, though potting material was not used in the simulation.

Figure 14D:
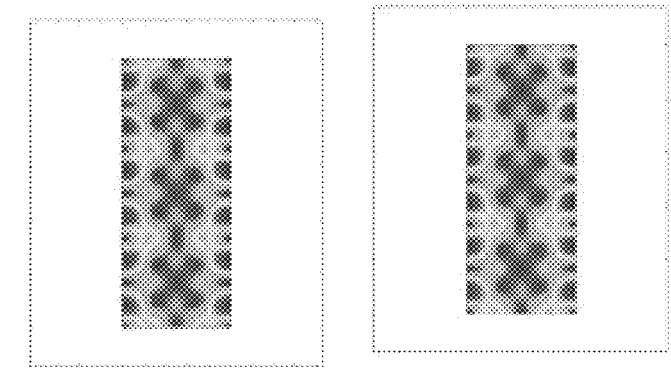
FIGS. 14A-14D are diagrams comparing the results of the numerical model (bottom) of FIG. 13 against published data (top), illustrating the accuracy of the numerical model.
Figure 14C:
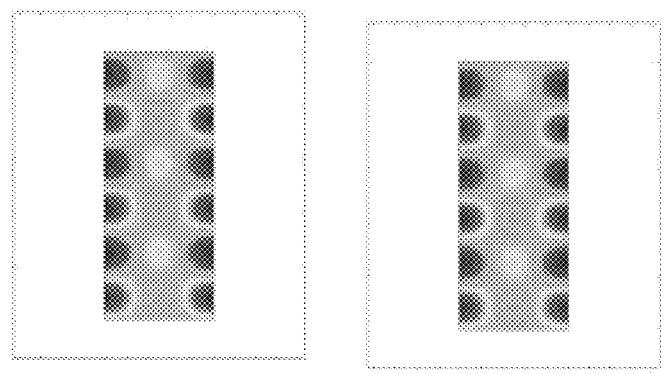
Figure 14B:
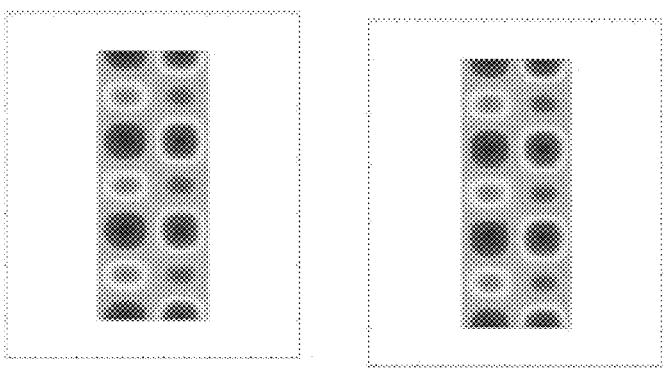
Figure 14A:
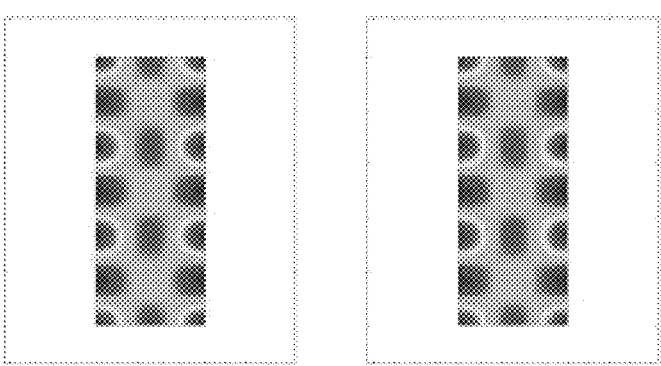

The simulation software was run, and its output was compared to published data (Barmatz, *J. Acoust. Soc. Am.* 77, 928, 1985). FIG. 14A compares the acoustic potential U. FIG. 14B compares the x-component of the acoustic radiation force (ARF). FIG. 14C compares the y-component of the ARF. FIG. 14D compares the absolute value of the ARF. In these figures, the published data is on the top, while the numerical model results are on the bottom. As can be seen here, the results of the numerical model match the published data, which validates the numerical model and subsequent calculations made therefrom.

Three different simulations were then run to model the separation of SAE 30 oil droplets from water using three different piezoelectric transducers: a 1-element transducer (i.e. single crystal), a 4-element transducer, and a 5-element transducer. The transducers were operated at the same frequency, and the following parameters were used for the oil and the water: oil particle radius ($R_p$)=10 μm; oil density ($\rho_p$)=865 kg/m$^3$; speed of sound in oil ($c_p$)=1750 m/sec; particle velocity ($\mu_f$)=0.001 kg/m·sec; water density ($\rho_f$)= 1000 kg/m$^3$; and speed of sound in water ($c_f$)=1500 m/sec.

For the 4-element transducer, each channel had a width of 0.0156 inches and a depth of 0.0100 inches, and each element had a width of 0.2383 inches (total width of the transducer was one inch). For the 5-element transducer, each channel had a width of 0.0156 inches and a depth of 0.0100 inches, and each element had a width of 0.1875 inches.

FIG. 15 shows the simulation of the forces on a particle using the 1-element transducer, which is a two-dimensional representation of PZT crystal 200. FIG. 16 shows the simulation of the forces on a particle using the 4-element transducer, which is a two-dimensional representation of PZT crystal 200'. FIG. 17 shows the simulation of the forces on a particle using the 5-element transducer, which is a two-dimensional representation of PZT crystal 200". Each transducer had the same width, regardless of the number of elements. The amplitude of the multi-dimensional acoustic standing waves generated therefrom are clearly seen (lighter area is higher amplitude than darker area).

Next, simulations were run on a 4-element array to compare the effect of the phase on the waves. The flow rate was 500 mL/min, the Reynolds number of the fluid was 220, the input voltage per element was 2.5 VDC, and the DC power per element was 1 watt. In one simulation, the four elements were in a 0-180-0-180 phase (i.e. out of phase) with respect to each other. In another simulation, the four elements were all in phase with each other. The simulations were then compared to actual experiments conducted with a transducer device having a 4×4 piezoelectric array as in FIG. 18. The transducer in FIG. 18 is configurable to be rotatable, whereby the Piezoelectric array can be rotated during operation.

Figure 18:
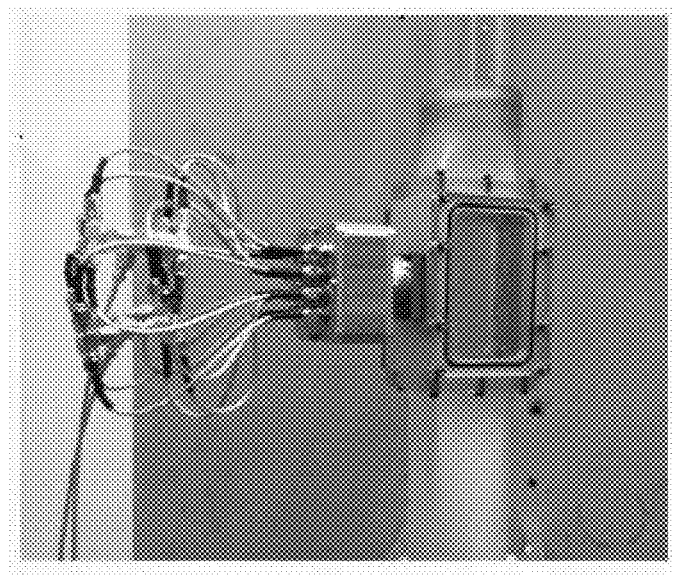
FIG. 18 is a picture of an acoustophoretic setup with a 4×4 piezoelectric array made from a 2 MHz PZT-8 crystal with kerfs made in the crystal, as shown in FIG. 5.
Figures 19, 20:
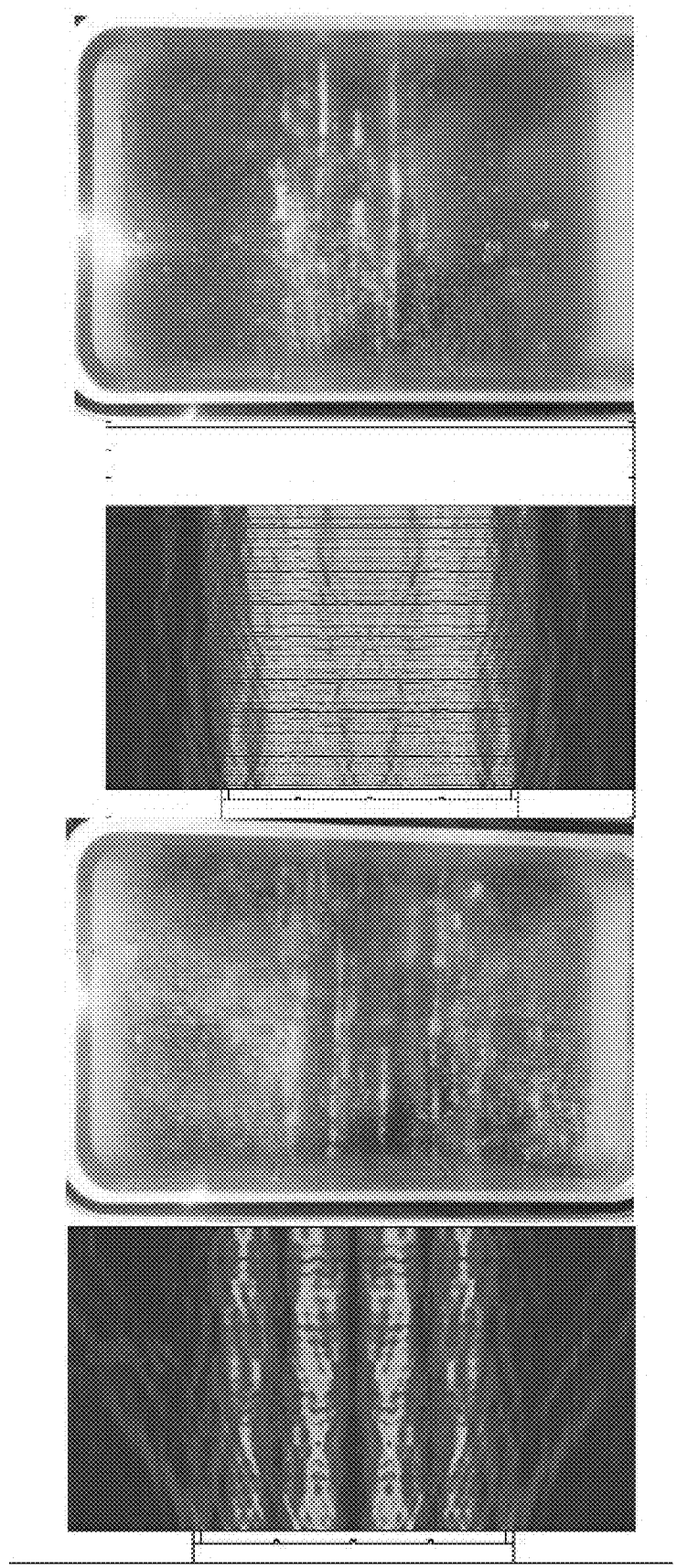
FIG. 19 is a comparison of the simulation of an out-of-phase piezoelectric array with an actual acoustophoretic experiment using the out-of-phase array. For this simulation, out-of-phase refers to the phase angle of the delivered voltage. For out-of-phase testing, the phasing varied from 0°-180°-0°-180° for the numerical model. For the experimental test, the elements were varied in a checkerboard pattern.
FIG. 20 is a comparison of the simulation of an in-phase piezoelectric array with an actual acoustophoretic experiment using the in-phase array. For this simulation, in-phase refers to the phase angle of the delivered voltage. For in-phase testing, the phasing was kept constant between all elements.

FIG. 19 compares the results of the out-of-phase simulation (left) with a picture (right) showing the actual results when an out-of-phase array was used in the transducer device of FIG. 18. The results are very similar. Where the amplitude is high in the simulation, trapped particles are seen in the actual picture.

FIG. 20 compares the results of the in-phase simulation (left) with a picture (right) showing the actual results when an in-phase array was used in the transducer device of FIG. 18. The results are very similar.

Additional numerical models were performed with the 4-element transducer and the 5-element transducer, either in-phase or out-of-phase in different arrangements, as described in Table 3 below, over a frequency sweep of 2.19 MHz to 2.25 MHz, for oil droplets of diameter 20 microns. Out-of-phase means that adjacent elements are excited with different phases.

Figure 22:
FIG. 22 is a diagram showing the out-of-phase modes tested for the 4-element array.
Figure 23:
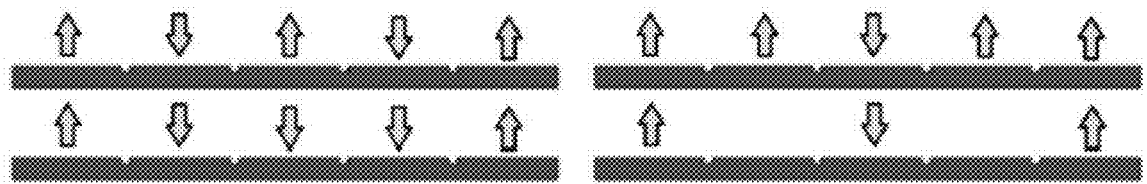
FIG. 23 is a diagram showing the out-of-phase modes tested for the 5-element array

FIG. 22 is a diagram illustrating the two out-of-phase modes that were simulated for the 4-element array. The left-hand side illustrates the 0-180-0-180 mode, while the right-hand side illustrated the 0-180-180-0 mode. FIG. 23 is a diagram illustrating the four out-of-phase modes that were simulated for the 5-element array. The top left picture illustrates the 0-180-0-180-0 mode. The top right picture illustrates the 0-0-180-0-0 mode. The bottom left picture illustrates the 0-180-180-180-0 mode. The bottom right picture illustrates the 0-90-180-90-0 mode.

The ratio of the lateral (x-axis) force component to the axial (y-axis) force component of the acoustic radiation force was determined over this frequency range, and the range of that ratio is listed in Table 3 below.

TABLE 3

| Transducer | Phase | Ratio Min | Ratio Max |
|---|---|---|---|
| 1-Element (single crystal) | | ~0.15 | ~0.75 |
| 4-Element Array | In-Phase | ~0.08 | ~0.54 |
| 4-Element Array | (0-180-0-180) | ~0.39 | ~0.94 |
| 4-Element Array | (0-180-180-0) | ~0.39 | ~0.92 |
| 5-Element Array | In-Phase | ~0.31 | ~0.85 |
| 5-Element Array | (0-180-0-180-0) | ~0.41 | ~0.87 |

TABLE 3-continued

| Transducer | Phase | Ratio Min | Ratio Max |
|---|---|---|---|
| 5-Element Array | (0-0-180-0-0) | ~0.41 | ~0.81 |
| 5-Element Array | (0-180-180-180-0) | ~0.40 | ~0.85 |
| 5-Element Array | (0-90-180-90-0) | ~0.38 | ~0.81 |

Figure 24:
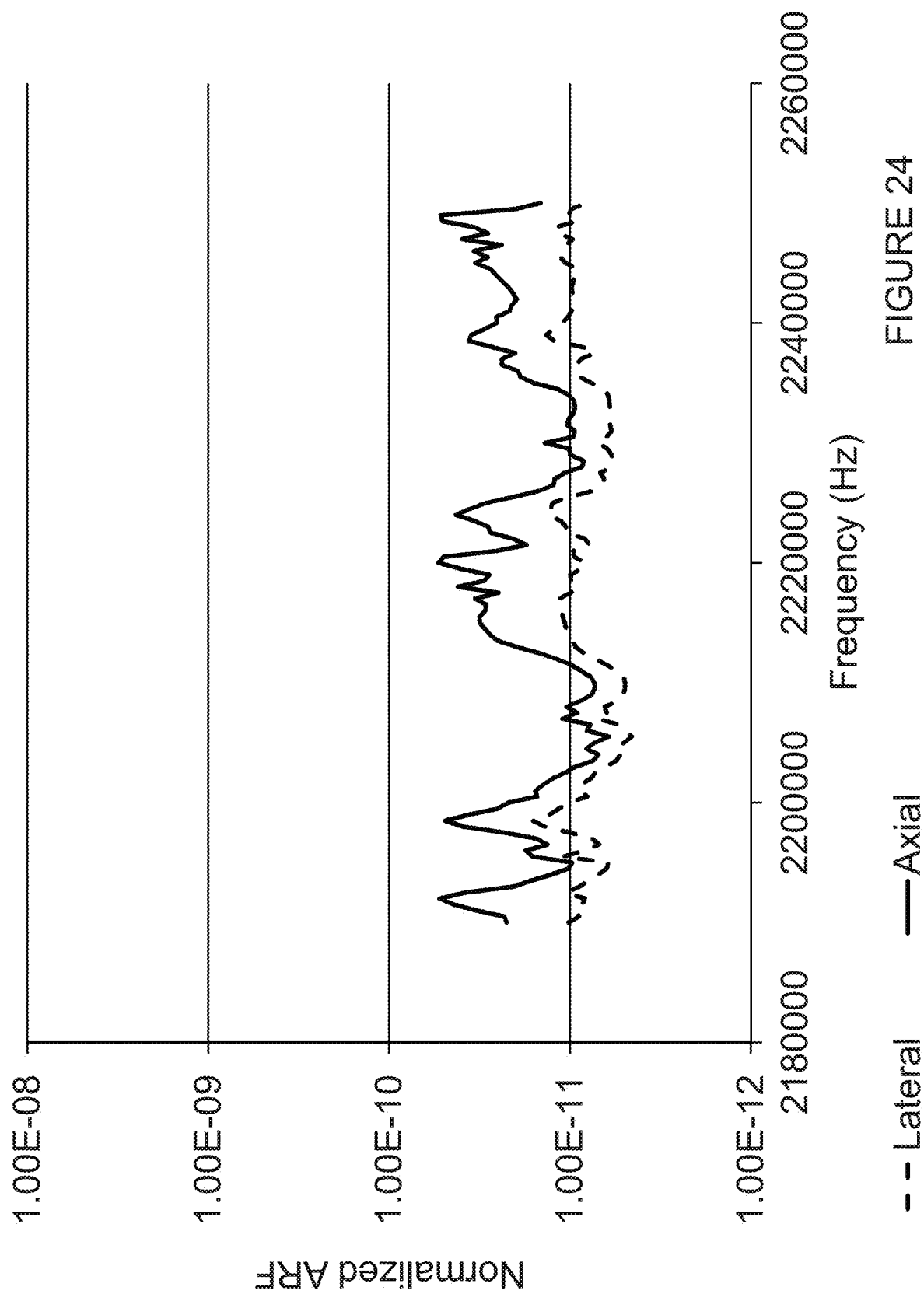
FIG. 24 is a graph showing the normalized acoustic radiation force (ARF) from a monolithic piezoelectric crystal simulation.
Figure 25:
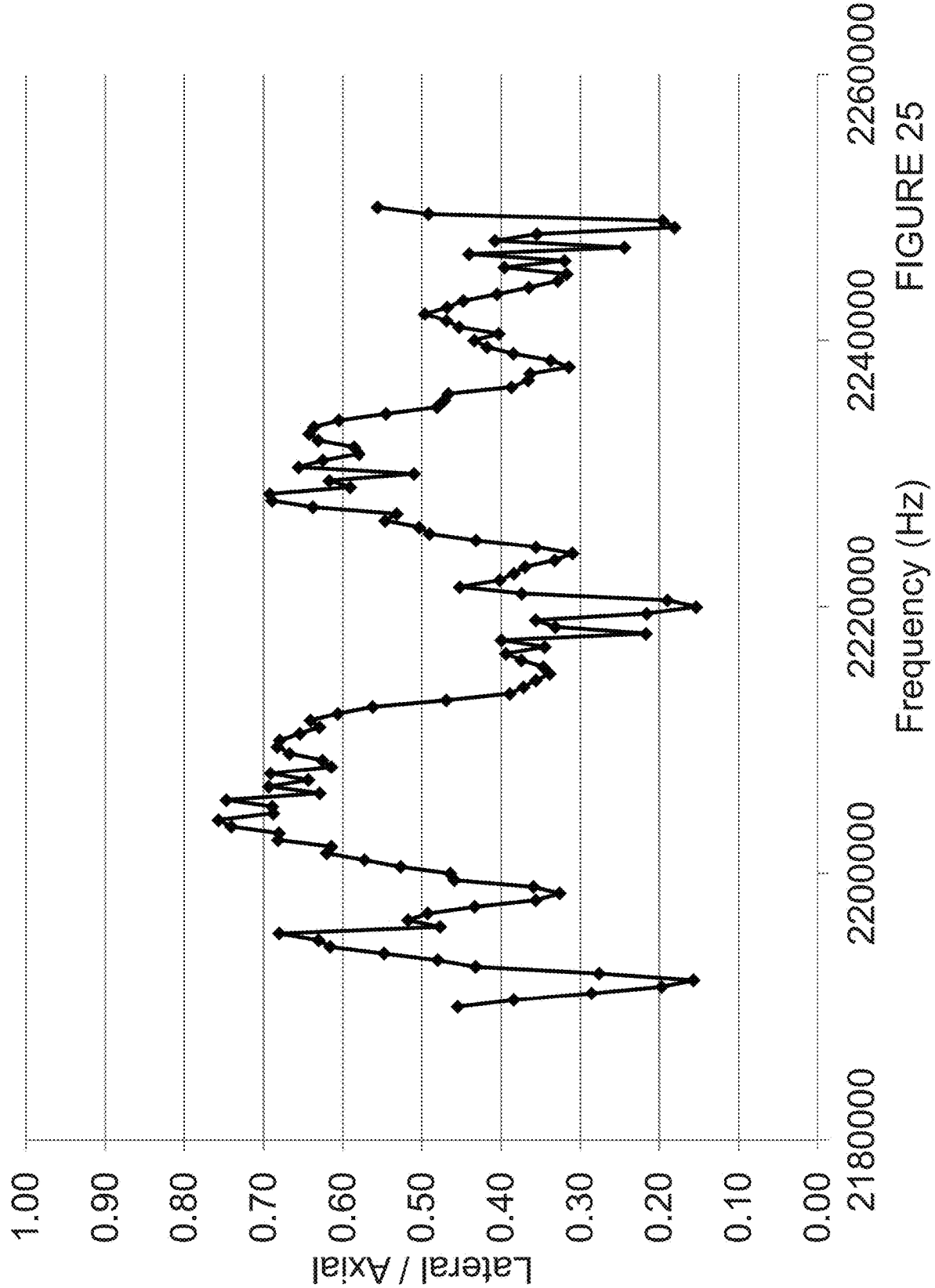
FIG. 25 is a graph showing the ratio of the ARF components (lateral to axial) for a monolithic piezoelectric crystal simulation.
Figure 26:
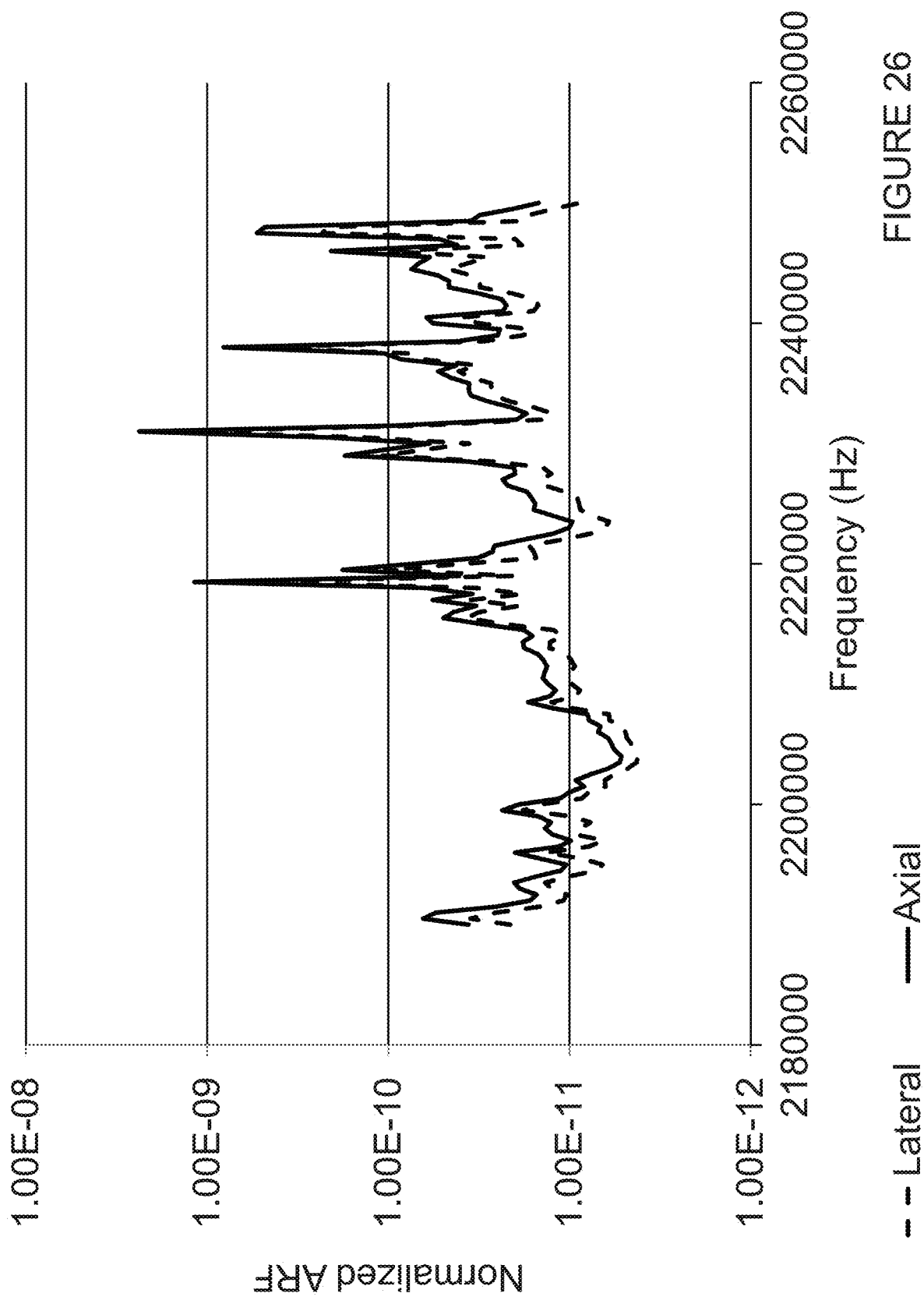
FIG. 26 is a graph showing the normalized acoustic radiation force (ARF) for a 5-element simulation with varying phasing.
Figure 27:
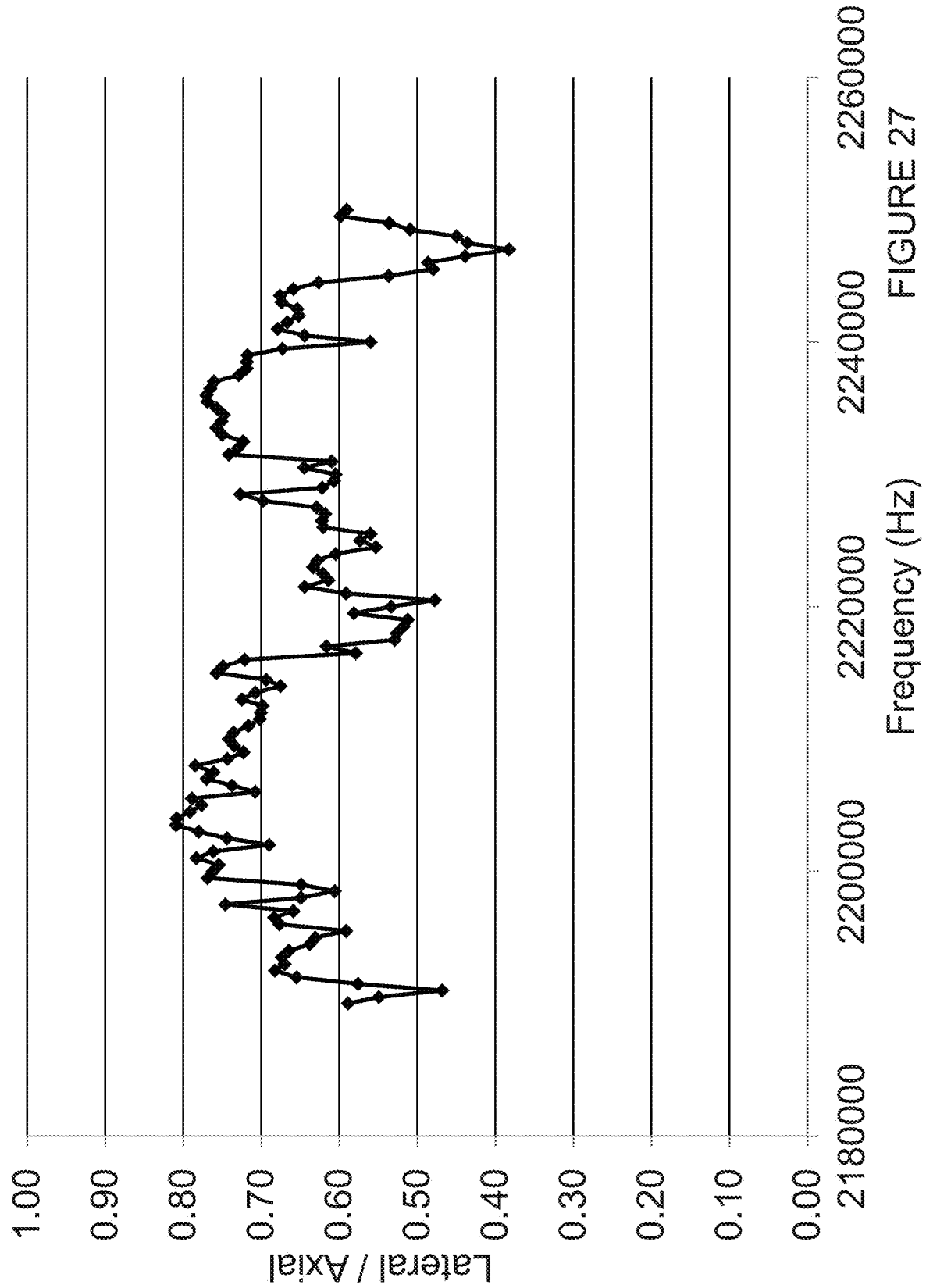
FIG. 27 is a graph showing the ratio of the ARF components (lateral to axial) for the 5-element simulation.

FIG. 24 shows the normalized acoustic radiation force (ARF) from the single piezoelectric crystal simulation. The ARF value was normalized with the real power calculated with the measured voltage and current. FIG. 25 shows the ratio of the ARF components (lateral to axial) for the single piezoelectric crystal simulation over the tested frequency range. FIG. 26 shows the normalized acoustic radiation force (ARF) from the 5-element simulation. FIG. 27 shows the ratio of the ARF components (lateral to axial) for the 5-element simulation over the tested frequency range. Comparing FIG. 24 to FIG. 26, the peak ARF for the 1-element simulation is about 6e−11, while the peak ARF for the 5-element simulation is about 2e−9. Comparing FIG. 25 to FIG. 27, the ratio of the forces are also more consistent, with a variation of about 0.60 compared to about 0.40.

Generally, the 4-element and 5-element arrays produced high ratios, including some greater than 0.9. Some of the simulations also had acoustic radiation force amplitudes that were almost two orders of magnitude higher than those produced by the 1-element transducer (which served as the baseline).

Figure 28:
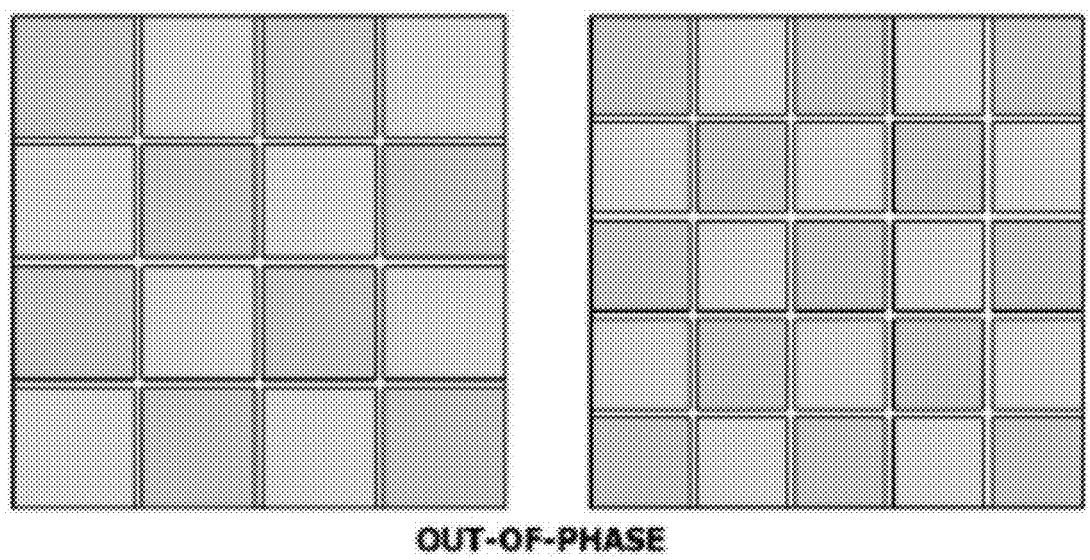
FIG. 28 is a diagram showing the phasing of the arrays during out-of-phase testing. Dark elements had a 0° phase angle and light element had a 180° phase angle when tested
Figure 29:
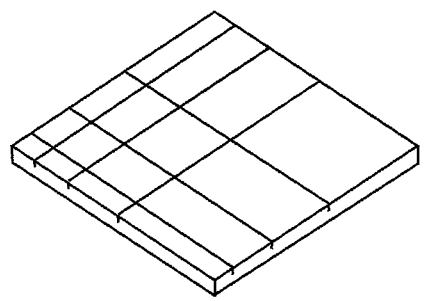
FIG. 29 is an isometric view of a piezoelectric array with elements arranged in a non-uniform pattern.
Figure 30:
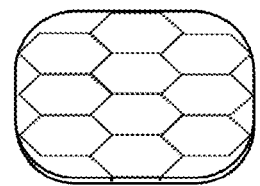
FIG. 30 is an isometric view of a piezoelectric array with elements arranged in a honeycomb pattern.
Figure 31:
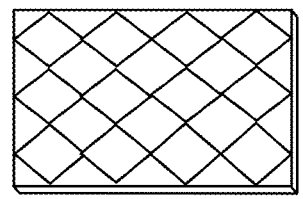
FIG. 31 is an isometric view of a piezoelectric array with elements arranged in a diamond pattern.

Experimental 16-element arrays and 25-element arrays were then tested. The feed solution was a 3% packed cell mass yeast solution, used as a simulant for CHO cells for biological applications. For out-of-phase testing, a checkerboard pattern of 0° and 180° phases was used. For the 25-element array, 12 elements were at 180° and 13 elements were at 0°. These checkerboard patterns are illustrated in FIG. 28. The left-hand side is the 16-element array and the right-hand side is the 25-element array, with the different shades indicating the different phase angle.

The turbidity of the feed, concentrate, and permeate were measured after 30 minutes at various frequencies. The concentrate was the portion exiting the device that contained the concentrated yeast, along with some fluid. The permeate was the filtered portion exiting the device, which was mostly liquid with a much lower concentration of yeast. A lower turbidity indicated a lower amount of yeast. The capture efficiency was determined as (feed-permeate)/feed*100%. The feed rate was 30 mL/min, and the concentrate flow rate was 5 mL/min. The power to the transducers was set at 8 W.

Table 4 lists results for the single-element transducer, which is used as a baseline or control.

TABLE 4

| | Frequency (MHz) | |
|---|---|---|
| | 2.225 | 2.244 |
| Concentrate (NTU) | 15,400 | 15,400 |
| Permeate (NTU) | 262 | 327 |
| Feed (NTU) | 4,550 | 5,080 |
| Capture Efficiency (%) | 94.2 | 93.6 |

Table 5 lists results for the 16-element in-phase experiments.

TABLE 5

| | Frequency (MHz) | | | | | | | |
|---|---|---|---|---|---|---|---|---|
| | 2.22 | 2.225 | 2.23 | 2.242 | 2.243 | 2.244 | 2.255 | 2.26 |
| Concentrate (NTU) | 22,700 | 24,300 | 22,500 | 24,600 | 23,100 | 28,100 | 27,400 | 23,800 |
| Permeate (NTU) | 205 | 233 | 241 | 201 | 249 | 197 | 244 | 165 |
| Feed (NTU) | 5,080 | 4,850 | 5,100 | 4,830 | 4,810 | 5,080 | 4,940 | 4,830 |
| Capture Efficiency (%) | 96.0 | 95.2 | 95.3 | 95.8 | 94.8 | 96.1 | 95.1 | 96.6 |

Table 6 lists results for the 16-element out-of-phase experiments.

TABLE 6

| | Frequency (MHz) | | | | | | | |
|---|---|---|---|---|---|---|---|---|
| | 2.22 | 2.225 | 2.23 | 2.242 | 2.243 | 2.244 | 2.255 | 2.26 |
| Concentrate (NTU) | 40,900 | 21,400 | 26,000 | 49,300 | 19,100 | 55,800 | 22,100 | 35,000 |
| Permeate (NTU) | 351 | 369 | 382 | 1,690 | 829 | 761 | 397 | 581 |
| Feed (NTU) | 5,590 | 4,870 | 5,860 | 5,160 | 5,040 | 4,870 | 4,800 | 5,170 |
| Capture Efficiency (%) | 93.7 | 92.4 | 93.5 | 67.2 | 83.6 | 84.4 | 91.7 | 88.8 |

Comparing the 16-element array results to each other and the control, the in-phase array maintains high capture efficiency through the frequency range, while the out-of-phase array drops off quickly around 2.24 MHz. The efficiency results are very similar to the control for most in-phase tests. The in-phase efficiency was higher than the out-of-phase efficiency at every frequency.

Table 7 lists results for the 25-element in-phase experiments.

TABLE 7

| | Frequency (MHz) | | | | | | | |
|---|---|---|---|---|---|---|---|---|
| | 2.2190 | 2.2300 | 2.2355 | 2.2470 | 2.2475 | 2.2480 | 2.2485 | 2.2615 |
| Concentrate (NTU) | 13,300 | 19,800 | 20,900 | 21,400 | 13,700 | 17,300 | 19,000 | 19,500 |
| Permeate (NTU) | 950 | 669 | 283 | 1,044 | 1,094 | 1,164 | 688 | 797 |
| Feed (NTU) | 4,930 | 4,930 | 4,910 | 5,010 | 4,950 | 5,220 | 5,010 | 5,110 |
| Capture Efficiency (%) | 80.7 | 86.4 | 94.2 | 79.2 | 77.9 | 77.7 | 86.3 | 84.4 |

Table 8 lists results for the 25-element out-of-phase experiments.

TABLE 8

| | Frequency (MHz) | | | | | | | |
|---|---|---|---|---|---|---|---|---|
| | 2.2190 | 2.2300 | 2.2355 | 2.2470 | 2.2475 | 2.2480 | 2.2485 | 2.2615 |
| Concentrate (NTU) | 14,605 | — | 21,700 | 18,025 | 23,425 | 22,575 | 21,900 | 22,450 |
| Permeate (NTU) | 2,568 | 2,541 | 1,484 | 1,134 | 1,005 | 987 | 905 | 2,034 |
| Feed (NTU) | 5,610 | 6,020 | 5,200 | 6,010 | 5,880 | 5,840 | 5,860 | 5,880 |
| Capture Efficiency (%) | 54.2 | 57.8 | 71.5 | 81.1 | 82.9 | 83.1 | 84.6 | 65.4 |

Comparing the 25-element array results to each other and the control, both arrays are less efficient than the control. The 25-element in-phase array peaks around 95% and then drops off in both directions. The out-of-phase array peaks around 85% efficiency and drops off sharply. The efficiency results are very similar to the control. It should be noted that the high peak amplitudes found using the numerical model have not been tested experimentally.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. An apparatus for separating a second fluid or a particulate from a host fluid, comprising:
   a flow chamber that includes at least one inlet and at least one outlet;
   at least one ultrasonic transducer coupled to the flow chamber and including a piezoelectric array formed from a plurality of piezoelectric elements, and at least one of the piezoelectric elements being configured to be excited to vibrate in a higher order mode to generate a multi-dimensional acoustic standing wave in the flow chamber; and
   wherein the piezoelectric elements are arranged in a uniform or non-uniform pattern.

2. The apparatus of claim 1, further comprising at least one reflector across the flow chamber from the at least one ultrasonic transducer.

3. The apparatus of claim 1, wherein the piezoelectric array is present on a single crystal, with one or more channels separating the piezoelectric elements from each other.

4. The apparatus of claim 1, wherein each piezoelectric element is physically separated from surrounding piezoelectric elements by a potting material.

5. The apparatus of claim 1, wherein each piezoelectric element is connected to an individual electrode, such that each piezoelectric element can be individually controlled for phasing, frequency, and power.

6. The apparatus of claim 5, wherein the plurality of piezoelectric elements also share a common ground electrode.

7. The apparatus of claim 1, wherein the piezoelectric array can be rotated during operation.

8. The apparatus of claim 1, wherein the piezoelectric elements are arranged in a brick pattern, a honeycomb pattern, or a diamond pattern.

9. The apparatus of claim 1, wherein the at least one ultrasonic transducer comprises:
 a housing having a top end, a bottom end, and an interior volume; and
 the plurality of piezoelectric elements at the bottom end of the housing, each of the plurality of piezoelectric elements having an exterior surface and an interior surface; and
 an air gap between the plurality of piezoelectric elements and the top end of the housing.

10. The apparatus of claim 9, wherein the exterior surface of each piezoelectric element is covered by a wear surface material with a thickness of a half wavelength or less, the wear surface material being a urethane or silicone coating.

11. The apparatus of claim 1, wherein each piezoelectric element has no backing layer or wear layer.

12. A method of separating a second fluid or a particulate from a host fluid, comprising:
 flowing a mixture of the host fluid and the second fluid or particulate through an apparatus, the apparatus comprising:
  a flow chamber that includes at least one inlet and at least one outlet; and
  at least one ultrasonic transducer coupled to the flow chamber and including a piezoelectric array formed from a plurality of piezoelectric elements; and
  at least one of the piezoelectric elements being configured to be excited to vibrate in a higher order mode to generate a multi-dimensional acoustic standing wave in the flow chamber; and
 exciting the at least one ultrasonic transducer to generate the multi-dimensional acoustic standing wave in the flow chamber to separate the second fluid or particulate from the host fluid;
 wherein an axial force component aligned in a direction of propagation of the multi-dimensional acoustic standing wave and a lateral force component aligned in a direction transverse to the direction of propagation of the multi-dimensional acoustic standing wave are of the same order of magnitude.

13. The method of claim 12, wherein the apparatus further comprises at least one reflector across the flow chamber from the at least one ultrasonic transducer.

14. The method of claim 12, wherein the particulate is monoclonal antibodies recombinant proteins, Chinese hamster ovary (CHO) cells, NS0 hybridoma cells, baby hamster kidney (BHK) cells, or human cells; T cells, B cells, or NK cells; peripheral blood mononuclear cells (PBMCs); algae or other plant cells, bacteria, viruses, or microcarriers.

15. The method of claim 12, wherein the flow rate of the host fluid through the flow chamber is at least 40 mL/min.

16. The method of claim 12, wherein each piezoelectric element is individually driven at a frequency, the array having varying frequencies.

17. The method of claim 12, wherein the piezoelectric array is present on a single crystal, with one or more channels separating the piezoelectric elements from each other.

18. The method of claim 12, wherein each piezoelectric element is physically separated from surrounding piezoelectric elements by a potting material.

* * * * *